(12) United States Patent
An et al.

(10) Patent No.: US 10,849,568 B2
(45) Date of Patent: Dec. 1, 2020

(54) SYSTEMS AND METHODS FOR SYNCOPE DETECTION AND CLASSIFICATION

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Amy Jean Brisben, Saint Paul, MN (US); Jeffrey E. Stahmann, Ramsey, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 201 days.

(21) Appl. No.: 15/978,963

(22) Filed: May 14, 2018

(65) Prior Publication Data

US 2018/0325466 A1 Nov. 15, 2018

Related U.S. Application Data

(60) Provisional application No. 62/506,341, filed on May 15, 2017.

(51) Int. Cl.
*A61B 5/04* (2006.01)
*A61B 5/00* (2006.01)
(Continued)

(52) U.S. Cl.
CPC .......... *A61B 5/7282* (2013.01); *A61B 5/1116* (2013.01); *A61B 5/4094* (2013.01); *A61B 5/686* (2013.01); *A61B 5/7264* (2013.01); *A61B 7/00* (2013.01); *A61B 7/04* (2013.01); *A61B 5/0031* (2013.01); *A61B 5/0205* (2013.01); *A61B 5/04012* (2013.01); *A61B 5/0456* (2013.01);
(Continued)

(58) Field of Classification Search
None
See application file for complete search history.

(56) References Cited

U.S. PATENT DOCUMENTS

2010/0056929 A1* 3/2010 Stahmann ............ A61B 5/0031
600/484
2010/0228103 A1* 9/2010 Schecter .............. A61B 5/4094
600/301

(Continued)

OTHER PUBLICATIONS

Moya, Angel, et al., "Guidelines for the diagnosis and management of syncope", European Heart Journal (2009) 30, (2009), 2631-2671.

(Continued)

*Primary Examiner* — Ankit D Tejani
(74) *Attorney, Agent, or Firm* — Schwegman Lundberg & Woessner, P.A.

(57) ABSTRACT

Systems and methods for monitoring patient for syncope are discussed. A syncope monitor system can detect a precipitating event associated with a syncope onset, and acquire hemodynamic data in response to the detection of the precipitating event. A syncope analyzer circuit may generate temporal profiles of one or more hemodynamic parameters using the hemodynamic data. The syncope analyzer may use the temporal profiles to detect a syncopal event and to classify the syncopal event into one of a plurality of syncope categories. The detection and classification information may be output to a user or a process.

20 Claims, 8 Drawing Sheets

(51) Int. Cl.
*A61B 7/04* (2006.01)
*A61B 7/00* (2006.01)
*A61B 5/11* (2006.01)
*A61B 5/0205* (2006.01)
*A61B 5/145* (2006.01)
*A61B 5/0456* (2006.01)
*A61B 5/0472* (2006.01)

(52) U.S. Cl.
CPC ......... *A61B 5/0472* (2013.01); *A61B 5/14542* (2013.01)

(56) References Cited

U.S. PATENT DOCUMENTS

| | | | | |
|---|---|---|---|---|
| 2011/0021928 A1* | 1/2011 | Giovangrandi | ........ | G16H 50/20 600/484 |
| 2011/0061647 A1* | 3/2011 | Stahmann | ............ | A61B 5/0031 128/202.16 |

OTHER PUBLICATIONS

Sun, Benjamin C., et al., "Direct Medical Costs of Syncope-Related Hospitalizations in the United States", Am Journal of Cardiology, vol. 95, (Mar. 1, 2005), 668-671.

* cited by examiner

SYSTEMS AND METHODS FOR SYNCOPE DETECTION AND CLASSIFICATION

CLAIM OF PRIORITY

This application claims the benefit of priority under 35 U.S.C. § 119(e) of U.S. Provisional Patent Application Ser. No. 62/506,341, filed on May 15, 2017, which is herein incorporated by reference in its entirety.

TECHNICAL FIELD

This document relates generally to medical devices, and more particularly, to systems, devices and methods for detecting and classifying syncope.

BACKGROUND

Syncope is an abrupt loss of consciousness with a concomitant loss of postural tone. The loss of consciousness during syncope may be transient, usually accompanied by falling, followed by spontaneous, complete, and usually prompt recovery without intervention. Approximately 1 to 3 percent of emergency department visits and 6 percent of hospital admissions involve syncope, and 20 to 50 percent of adults experience one or more episodes during their lives. Patients presenting with a history of blackouts, faints or collapse usually require evaluation to assess the precise cause or nature of syncope. This is essential so as to assess both the risk of a serious underlying disorder, the risk of recurrent syncope, and subsequent injury.

Decreased cerebral perfusion is common to all causes of syncope. Positional change from supine to erect causes a 300- to 800-milliliter shift in blood volume from the thoracic cavity to the lower extremities. In healthy adults, cerebrovascular autoregulation ensures that cerebral blood flow remains within a narrow range independent of systemic blood pressure. However, older patients and those with chronic hypertension or cardiovascular diseases may be susceptible to syncope when a relatively small decrease in systemic blood pressure occurs.

Based on the underlying causes, syncope can be classified into three major types: cardiogenic, orthostatic, and neurally mediated syncope. Cardiogenic syncope is associated with significantly higher rates of morbidity and mortality than other causes. Patients with underlying cardiac disease, such as cardiac arrhythmias or structural cardiopulmonary diseases, are at higher risk for recurrent syncope than are other syncope patients. Patients with syncope are more likely to have coronary artery or cerebrovascular disease and to take cardiac or antihypertensive medications than patients without syncope. Orthostatic syncope is associated with orthostatic hypotension, characterized by a drop in blood pressure of at least 20 millimeters of mercury (mmHg) systolic or 10 mmHg diastolic within about three minutes of standing. Tachycardia and a heart rate greater than 100 beats per minute during testing indicate volume depletion. Minimal cardiac acceleration suggests baroreflex impairment may contribute to orthostatic syncope. Neurally mediated syncope is a disorder of the autonomic regulation of postural tone, and may be related to vasovagal, carotid sinus, or situational causes of hypotension. In healthy subjects, upon positional change, a series of complex neurohormonal events would maintain cerebral perfusion. For example, decreased venous return and subsequent decreased left ventricular filling may result in increased sympathetic tone and a hypercontractile left ventricle. However, overly sensitive left ventricular receptors may misinterpret hypercontractility as volume overload and falsely inhibit sympathetic stimulation while promoting parasympathetic drive, resulting in hypotension and syncope.

Syncope may be evaluated using various clinical tests. For example, cardiogenic syncope may be evaluated using electrocardiographic monitoring, echocardiography, or exercise stress testing. Tests for neurally mediated syncope may include head-up tilt-table test. Other tests, such as head computed tomography, magnetic resonance imaging, carotid and transcranial ultrasonography, and electroencephalography may be performed to detect cerebrovascular causes of syncope. Implantable monitors, such as implantable loop recorders (ILRs), may monitor a patient for syncope in an ambulatory setting, and record patient physiological data for further evaluation or risk stratification.

Overview

In-clinic tests for syncope evaluation aims at diagnosing causes and nature of a syncope episode that occurred in the past. Such post-syncope evaluation may not completely uncover the actual pathophysiology at the time of syncope. For example, the orthostatic challenge that attempts to mimic the orthostatic hypotension may not adequately reproduce the hemodynamic profile of the past spontaneous syncopal event from onset to full development. The tilt table test may have substantial false negative rate for detecting syncope onset in a clinical test.

Many syncopal events occur abruptly and unexpectedly. Compared to the in-clinic testing, ambulatory monitoring of patient at risk of syncope may be desired to detect spontaneous syncope or presyncope. Ambulatory syncope monitors, such as ILRs, typically continuously monitor patient cardiac electrical activity such as electrocardiogram (ECG), and detect syncope or presyncope if the cardiac electrical activity becomes abnormal. The patient or healthcare providers may be alerted to take proper precaution before syncope attack to prevent from fainting, falling, or injuries.

Currently, ambulatory monitors for syncope detection or evaluation, such as ILRs, are implanted for patients with documented history of syncope, such as recurrent or unexplained syncopal episodes. Because the ambulatory monitors typically monitor patient cardiac electrical activity, they are largely implanted to recognize, or rule out, cardiogenic syncope. However, in certain patients such as those with infrequent symptoms, syncope diagnosis using the cardiac electrical activity based monitor may be inadequate due to a low symptom-ECG correlation. Additionally, while syncope with cardiac causes constitutes only approximately 15 percent of overall syncope population, the majority of syncope are non-cardiac in nature, including about 60 percent being neurally mediated syncope, and about 15 percent being orthostatic syncope. Unexplained syncope, or syncope of unknown origin, is a syncope for which no clear explanation has been found after a conventional workup, and heavily affect the cost of medical care. Ambulatory cardiac monitors such as ILRs may not provide adequate differential diagnosis of the majority of non-cardiac or unexplained syncope, such as the orthostatic syncope or neurally mediated syncope. Furthermore, the ambulatory syncope monitors usually have limited battery power, storage, computing and information processing power, or communication bandwidth. The constraints in resource may affect the performance of syncope detection and evaluation especially when chronic hemodynamic monitoring and sophisticated information processing are desired. For these reasons, the present inventors have recognized that there remains a need for improved systems, devices, and methods for ambulatory monitoring patient for detecting and evaluating syncope.

This document discusses, among other things, systems, devices, and methods for monitoring a patient for syncope. A patient monitor system may include a physiological event detector circuit configured to detect a precipitating event using a physiological signal sensed from a patient, and a hemodynamic sensor circuit configured to sense a hemodynamic signal. The precipitating event may be associated with a syncope onset. The system may include a syncope analyzer circuit that may detect a syncopal event, and classify the detected syncopal event into one of a plurality of syncope categories, such as a pre-syncope, a full-blown syncope, a cardiogenic syncope, orthostatic syncope, or neurally mediated syncope. A control circuit may trigger the hemodynamic sensor circuit to acquire hemodynamic data in response to the detection of the precipitating event, and to control the syncope analyzer circuit to detect and classify the syncopal event using the hemodynamic data. The system may include an output circuit for outputting the detected and classified syncopal event to a user or a process.

Example 1 is a system for monitoring a patient for syncope. The system comprise a physiological event detector circuit that may detect a precipitating event associated with a syncope onset using at least one physiological signal; a hemodynamic sensor circuit that may sense a hemodynamic signal; a syncope analyzer circuit that may detect a syncopal event and classify the detected syncopal event into one of a plurality of syncope categories; and a control circuit. The control circuit may be configured to, in response to the detection of the precipitating event: trigger the hemodynamic sensor circuit to acquire hemodynamic data from the sensed hemodynamic signal; and control the syncope analyzer circuit to detect and classify the syncopal event using the acquired hemodynamic data. The system includes an output circuit that may output the detected and classified syncopal event to a user or a process.

In Example 2, the subject matter of Example 1 optionally includes the syncope analyzer circuit that may generate a temporal profile of a hemodynamic parameter using the acquired hemodynamic data, and detect and classify the syncopal event using the temporal profile of the hemodynamic parameter.

In Example 3, the subject matter of Example 2 optionally includes the temporal profile of the hemodynamic parameter that may include an initial measurement of the hemodynamic parameter within a first time window subsequent to an onset of the precipitating event and a late measurement of the hemodynamic parameter within a second time window subsequent to the first time window.

In Example 4, the subject matter of any one or more of Examples 2-3 optionally includes the hemodynamic signal that may include a heart sound (HS) signal. The HS signal includes first (S1) and second (S2) heart sound components. The syncope analyzer circuit may be configured to generate one or more of a S1 temporal profile or a S2 temporal profile in response to the detection of the precipitating event, and detect and classify a syncopal event using the S1 temporal profile or the S2 temporal profile.

In Example 5, the subject matter of Example 4 optionally includes the hemodynamic signal that may include a heart rate (HR) signal. The syncope analyzer circuit may be configured to generate a HR temporal profile in response to the detection of the precipitating event, and detect and classify a syncopal event further using the HR temporal profile.

In Example 6, the subject matter of Example 4 optionally includes the S1 temporal profile that may include an initial S1 intensity change ($\Delta S1_I$) within a first time window subsequent to an onset of the precipitating event and a late S1 intensity change ($\Delta S1_L$) within a second time window subsequent to the first time window; the S2 temporal profile includes an initial S2 intensity change ($\Delta S2_I$) within the first time window and a late S2 intensity change ($\Delta S2_L$) within the second time window; and the syncope analyzer circuit is configured to detect and classify a syncopal event using one or more of $\Delta S1_I$, $\Delta S1_L$, $\Delta S2_I$, or $\Delta S2_L$.

In Example 7, the subject matter of Example 6 optionally includes the syncope analyzer circuit that may be configured to detect or classify the detected syncopal event using a comparison of an initial HS response vector to a late HS response vector. The initial HS response vector comprises $\Delta S1_I$ and $\Delta S2_I$, and the late HS response vector comprising $\Delta S1_L$ and $\Delta S2_L$.

In Example 8, the subject matter of Example 7 optionally includes the syncope analyzer circuit that may be configured to compute an angle between the initial HS response vector and the late HS response vector. The angle represents composite changes in S1 intensity and in S2 intensity from the first time window to the second time window subsequent to the precipitating event. The syncope analyzer circuit may classify the detected syncope as an orthostatic syncope if the computed angle falls within a first range, and classify the detected syncope as a neutrally mediated syncope if the computed angle falls within a different second range.

In Example 9, the subject matter of any one or more of Examples 3-8 optionally includes the syncope analyzer circuit that may be configured to compute a transition time from the initial measurement to the late measurement of the hemodynamic parameter, and classify the detected syncopal event further using the computed transition time.

In Example 10, the subject matter of any one or more of Examples 3-9 optionally includes the syncope analyzer circuit that may be configured to compute a transition trajectory from the initial measurement to the late measurement of the hemodynamic parameter, and classify the detected syncopal event further using the computed transition trajectory. The transition trajectory may include at least one intermediate measurement of the hemodynamic parameter measured after the first time window and before the second time window.

In Example 11, the subject matter of any one or more of Examples 2-10 optionally includes the hemodynamic signal that may include a photoplethysmogram (PPG) signal. The syncope analyzer circuit may be configured to generate a temporal profile of a PPG parameter using the PPG signal, and detect and classify a syncopal event using the temporal profile of the PPG parameter.

In Example 12, the subject matter of any one or more of Examples 1-11 optionally includes the physiological event detector circuit that may be configured to detect a cardiac arrhythmia event using a cardiac electrical activity signal. The control circuit may trigger the hemodynamic sensor circuit to acquire the hemodynamic data in response to the detection of the cardiac arrhythmia event.

In Example 13, the subject matter of any one or more of Examples 1-12 optionally includes the physiological event detector circuit that may be configured to detect a postural change using a posture sensor signal. The control circuit may trigger the hemodynamic sensor circuit to acquire the hemodynamic data in response to a detection of a postural change to an upright posture.

In Example 14, the subject matter of any one or more of Examples 1-13 optionally includes the physiological event detector circuit that may be configured to detect a heart rate change and a postural change. The control circuit may trigger the hemodynamic sensor circuit to acquire the hemodynamic data in response to a detection of an acute reduction in heart rate accompanied by no substantial postural change.

In Example 15, the subject matter of any one or more of Examples 1-14 optionally includes the syncope analyzer circuit that may be configured to classify the detected syncopal event into one or more: a presyncope; a full-blown syncope; a cardiogenic syncope; a non-cardiogenic syncope; a neutrally mediated syncope; an orthostatic syncope; or a non-syncope.

Example 16 is a non-transitory machine-readable storage medium, comprising a plurality of instructions that, responsive to being executed with processor circuitry of a computing device, cause the computing device to: detect a precipitating event associated with a syncope onset using at least one physiological signal; acquire hemodynamic data in response to the detection of the precipitating event; detect a syncopal event using the acquired hemodynamic sensor data; classify the detected syncopal event into one of a plurality of syncope categories using the acquired hemodynamic sensor data.

In Example 17, the subject matter of Example 16 optionally includes an instruction that causes the computing device to generate a temporal profile of a hemodynamic parameter using the acquired hemodynamic data, and detect and classify the syncopal event using the temporal profile of the hemodynamic parameter.

Example 18 is a method for monitoring a patient for syncope using a syncope monitor. The method comprises: detecting, via a physiological event detector circuit, a precipitating event associated with a syncope onset using at least one physiological signal; acquiring hemodynamic data from the patient, via a hemodynamic sensor circuit, in response to the detection of the precipitating event; detecting a syncopal event via a syncope detector circuit using the acquired hemodynamic sensor data; classifying the detected syncopal event into one of a plurality of syncope categories via a syncope classifier circuit using the acquired hemodynamic sensor data; outputting the detected and classified syncopal event to a user or a process.

In Example 19, the subject matter of Example 18 optionally includes an initial measurement of the hemodynamic parameter within a first time window subsequent to an onset of the precipitating event; and a late measurement of the hemodynamic parameter within a second time window subsequent to the first time window. The detecting or classifying the syncopal event is by using the temporal profile of the hemodynamic parameter.

In Example 20, the subject matter of Example 19 optionally includes steps of: generating an initial heart sound (HS) response vector within a first time window subsequent to an onset of the precipitating event, the initial HS response vector comprising an initial S1 intensity change and an initial S2 intensity change; generating a late HS response vector within a second time window subsequent to the first time window, the late HS response vector comprising a late S1 intensity change and a late S2 intensity change. The detecting or classifying of the syncopal event includes comparing the initial HS response vector to the late HS response vector.

In Example 21, the subject matter of Example 18 optionally includes classifying the detected syncopal event, which may include one of more of: a presyncope; a full-blown syncope; a cardiogenic syncope; a non-cardiogenic syncope; a neutrally mediated syncope; an orthostatic syncope; or a non-syncope.

In Example 22, the subject matter of Example 18 optionally includes the precipitating event that may include one or more of: a cardiac arrhythmia event; a postural change to an upright posture; a sustained upright posture with physical inactivity; or an acute reduction in heart rate with no substantial postural change In Example 23, the subject matter of Example 18 optionally includes adjusting one or more parameters for sensing the hemodynamic signal or for acquiring hemodynamic data in response to the detection of the precipitating event.

The systems, devices, and methods discussed in this document may improve the technology of ambulatory monitoring and differential diagnosis of syncope. Conventional ambulatory syncope monitors base the syncope detection and assessment using patient cardiac electrical activities. These conventional monitors and methods may face challenges of less specific recognition of non-cardiac or unexplained syncope such as neurally mediated syncope or orthostatic syncope, which make up the majority of spontaneous syncope. The present document provides a technological improvement in ambulatory syncope monitoring and differential diagnosis, by utilizing, among other things, precipitating event-triggered patient hemodynamic monitoring in addition to the cardiac electrical activity to detect syncope and further to classify the syncopal event into different syncope types. The disclosed systems and methods that use the hemodynamic profiles may improve the sensitivity and specificity of syncope detection. This may not only ensure timely attention and medical intervention of syncope patient and thereby preventing further injuries subsequent to syncope, but may also avoid or reduce unnecessary medical interventions (e.g., drugs, procedures, or device therapies) scheduled, prescribed, or provided to patients who are identified to be free of syncope or at a low risk of developing future syncope. The syncope classification as described in this document may further help provide individualized therapy and patient management specific to the syncope type. As such, the devices and methods discussed herein would not only better align the medical resources to serve the need of more patients, but may also achieve overall system cost savings for chronically monitoring syncope patients.

The systems, devices, and methods discussed in this document may also improve functionality of a medical device or a patient management system. Among other things, the present document described a precipitating event-triggered hemodynamic data acquisition, storage, and analysis of syncopal events. The hemodynamic sensing and information processing may put a high demand for battery power, storage space, computing and process power, and communication bandwidth. The event-triggered hemodynamic sensing and syncope evaluation may reduce active operation time of the corresponding device components, and provide a power- and resource-conservative solution to ambulatory syncope monitoring with improved efficiency at lower operation cost.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring a patient for syncope. A precipitating event associated with a syncope onset may be detected, and used to trigger hemodynamic data acquisition. A syncope analyzer circuit may generate temporal profiles of one or more hemodynamic parameters in response to the detection of the precipitating event, and use the temporal profiles to detect a syncopal event and to classify the detected syncopal event into one of a plurality of syncope categories including cardiogenic, orthostatic, or neurally mediated syncope. The detection and classification information may be output to a user, or a process such as to initiate or adjust medical intervention.

Figure 1:
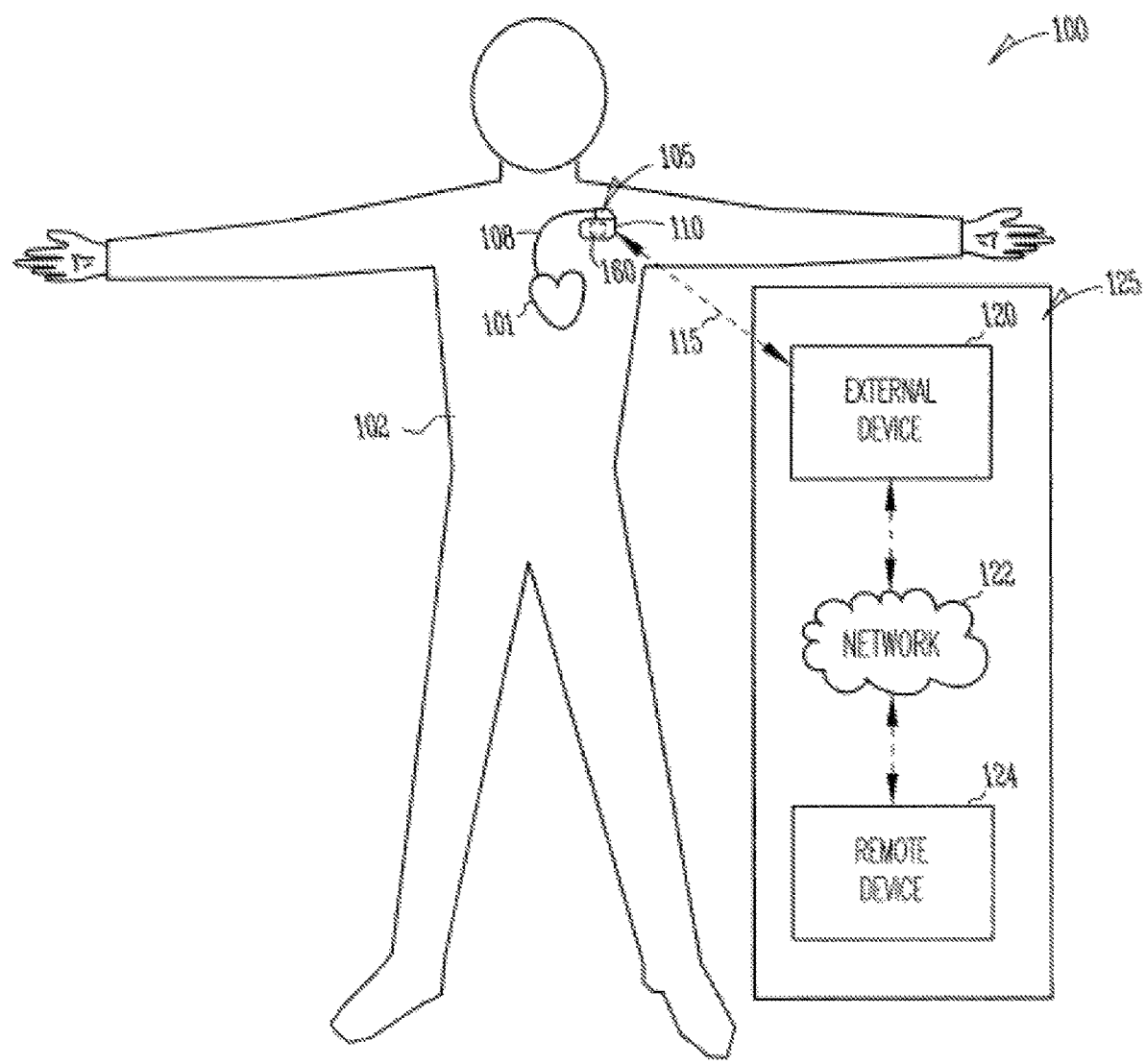
FIG. 1 illustrates generally an example of a patient monitor system and portions of an environment in which the system may operate.

FIG. 1 illustrates generally an example of a patient monitor system 100 and portions of an environment in which the system 100 may operate. The patient monitor system 100 may chronically monitor a patient 102 to detect and evaluate a syncopal event. Portions of the system 100 may be ambulatory. Portions of the system 100 may be disposed in the patient's home or office, a hospital, clinic, or physician's office. The patient monitor system 100 may include an ambulatory system 105 associated with the patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. The physiological signals may contain information about patient physiological response to a precipitating event associated with onset of a future syncopal event. The physiological signal may represent changes in patient hemodynamic status. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

The AMD 110 may include a syncope detection and analyzer circuit 160 for detecting a syncopal event using one or more physiological signals. Hemodynamic data acquisition may be initiated in response to a detection of a precipitating event, such as a cardiac arrhythmia, a reduction in heart rate, a postural change, a sustained upright posture, a blood pressure change, a thoracic impedance change, or a combination of two or more events. The syncope detection and analyzer circuit 160 may generate an indicator of hemodynamic profile indicating changes in cardiac contractility or blood pressure over time. The hemodynamic profile indicators may be used to detect syncope, or further to classify the detected syncope as one of a plurality of categories including presyncope, full-blown syncope, cardiogenic syncope, non-cardiogenic syncope, orthostatic syncope, or neurally mediated syncope, among other syncope types. Examples of the syncope detection and classification are discussed below, such as with reference to FIGS. 2-4.

The AMD 110 may include a therapy circuit that may generate and deliver a therapy to the patient. The therapy may be preventive (e.g., to prevent development into a full-blown), or therapeutic (e.g., to treat syncope or alleviate complications) in nature such as to modify, restore, or improve patient neural, cardiac, or respiratory functions. Examples of the therapy may include electrical, magnetic, or other forms of therapy. In some examples, the AMD 110 may include a drug delivery system such as a drug infusion pump device to deliver drug therapy to the patient to manage syncope. In some examples, the AMD 110 may monitor patient post-syncopal hemodynamic status for a specified sustained time period to assess long-term impact of syncope, or to assess the efficacy of an anti-syncopal therapy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to detect and classify syncope, or optionally delivering or adjusting a therapy to the patient 102. The external system 125 may communicate with the AMD 110 via the communication link 115. The device data received by the external system 125 may include real-time or stored physiological data from the patient 102, diagnostic data such as detected and classified syncope types, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi- or distributed computing and processing system. In an example, the remote device 124 may include a data processor configured to perform further syncope analysis, such as detection and classification of syncope, using the signals received by the AMD 110. Computationally intensive algorithms, such as machine-learning algorithms, may be implemented in the remote device 124 to process the data retrospectively to analyze syncope, and to confirm, reject, or modify the syncope detection and classification information as provided by the AMD 110. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the syncope detection and classification information to a system user such as the patient or a clinician. The clinician may review, perform further analysis, or adjudicate the device detection and classification. The syncope detection and classification, optionally along with the physiological and hemodynamic data, may be output to a process including an instance of a computer program executable in a microprocessor. In an example, the process may include an automated generation of recommendations for initiating or adjusting a therapy, or a recommendation for further diagnostic test or treatment. In an example, the external device 120 or the remote device 124 may include a respective display unit for displaying the physiological and hemodynamic signals, or alerts, alarms, emergency calls, or other forms of warnings about the detection and classification of a syncopal event.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
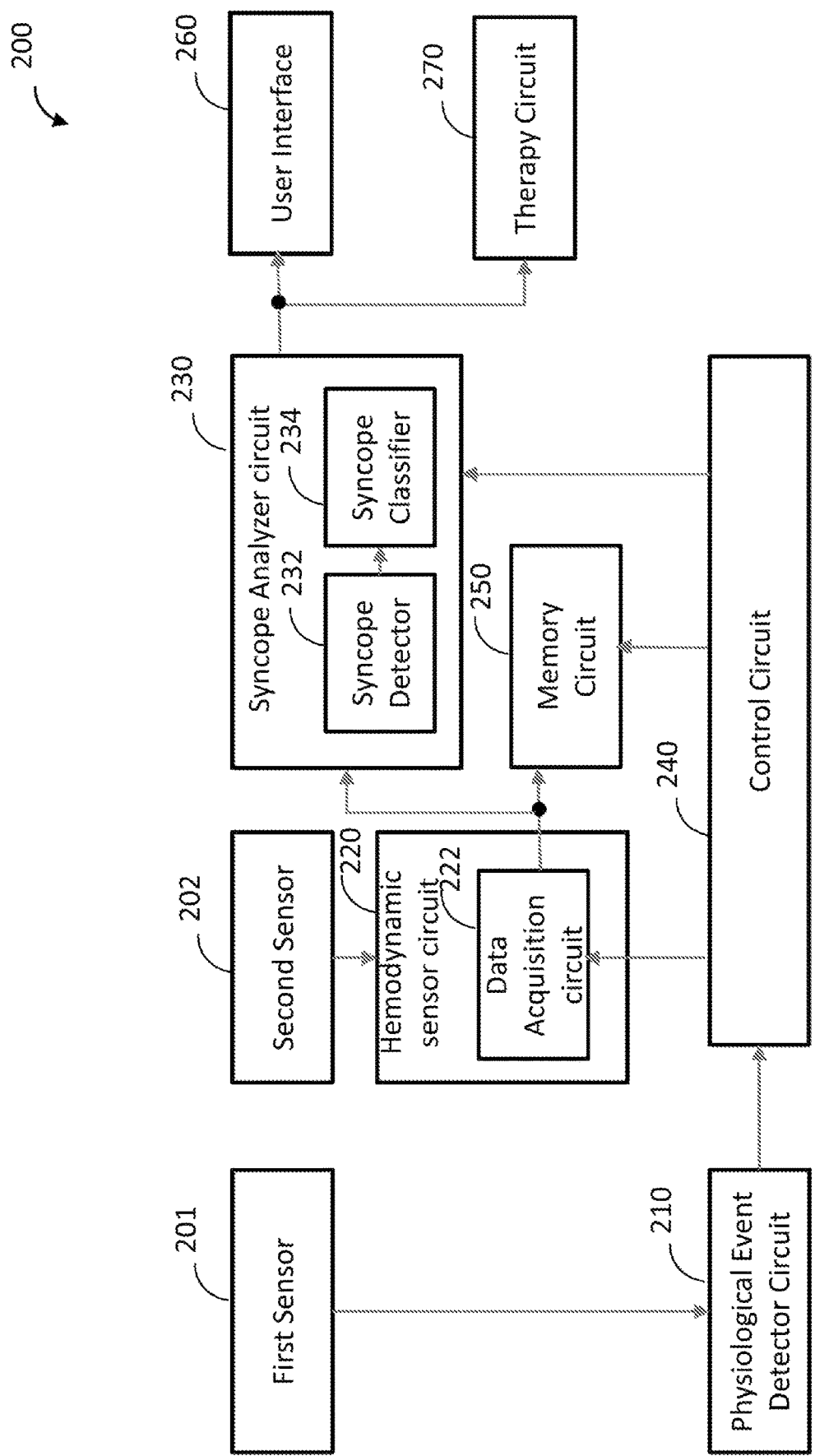
FIG. 2 illustrates generally an example of a syncope monitor system for detecting and evaluating syncope in a patient.

FIG. 2 illustrates generally an example of a syncope monitor system 200 that may be configured to detect and evaluate syncope in a patient. At least a portion of the syncope monitor system 200 may be implemented in the AMD 110, the external system 125 such as one or more of the external device 120 or the remote device 124, or distributed between the AMD 110 and the external system 125. As illustrated in FIG. 2, the syncope monitor system 200 may include one or more of a physiological event detector circuit 210, a hemodynamic sensor circuit 220, a syncope analyzer circuit 230, a control circuit 240, a memory circuit 250, and a user interface unit 260. The syncope monitor system 200 may include an optional therapy circuit 270 for delivering a therapy to treat syncope or alleviate complications or symptoms.

The physiological event detector circuit 210 may detect a precipitating event using at least one physiological signal.

The physiological event detector circuit 210 may include a sense amplifier circuit to sense the at least one physiological signal from a patient via a first sensor 201, such as an implantable, wearable, or otherwise ambulatory sensor or electrodes associated with the patient. The sensor may be incorporated into, or otherwise associated with an ambulatory device such as the AMD 110. In some examples, the physiological signals sensed from a patient may be stored in a storage device, such as an electronic medical record (EMR) system. The physiological event detector circuit 210 may be configured to receive a physiological signal from the storage device in response to a user input or triggered by a specific event, and detect a precipitating event from the received physiological signals. Examples of the physiological signals for detecting the precipitating event may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The physiological event detector circuit 210 may include one or more sub-circuits to digitize, filter, or perform other signal conditioning operations on the received physiological signal.

The precipitating event may be associated with a syncopal onset, such as an event that may lead to a certain type of syncope according to patient population data. The identified precipitating event may be further analyzed to determine if likely or unlikely to be associated with a particular type of syncope. In an example, the precipitating event may include a cardiac arrhythmia, such as a bradycardia, a tachycardia, a sinus pause or asystole, among others. A cardiac arrhythmia may be associated with or trigger a cardiogenic syncope. The physiological event detector circuit 210 may senses one or more cardiac electrical activity signals including surface ECG, subcutaneous ECG, or intracardiac EGM, and detect cardiac arrhythmia using heart rate, heart rate stability, cardiac signal waveform morphology, or other signal characteristics derived from the one or more cardiac electrical activity signals. In another example, the precipitating event may include a change in posture. For example, a sudden transition to an upright posture may produce gravitational pooling of blood in lower extremities, reduce venous return to the heart, and cause a reduction in stroke volume and decrease in blood pressure. In patients with inadequate autonomic response, the blood pressure can be adequately recover at least due to blunted baroreflex sensitivity. This may lead to orthostatic hypotension and syncope. The physiological event detector circuit 210 may senses via a posture sensor, or receive from a data storage device, a postural change to an upright posture. Examples of the posture sensor may include an accelerometer, a tilt switch, or a thoracic impedance sensor configured to detect a posture or position. In yet another example, the precipitating event may include an acute reduction in heart rate accompanied by no substantial postural change, or a sustained upright posture accompanied by physical inactivity. Neurally mediated syncope, such as vasovagal syncope, may be attributed to malfunction in the parts of the nervous system that regulate heart rate and blood pressure. Typical triggers for vasovagal syncope include prolonged standing or upright sitting and lack of physical activity, abrupt change in posture, stress, straining, or after or during urination, among others. Low heart rate and low blood pressure may lead to reduced cerebral perfusion, causing fainting and syncope. The physiological event detector circuit 210 may sense via one or more of a heart rate sensor, a posture sensor, or an activity sensor, acute reduction in heart rate accompanied by no substantial postural change, or a sustained upright posture accompanied by low physical activity. Other precipitating events may additionally or alternatively be detected, which include a venous pooling in legs, a reduction in venous return, a reduction of cardiac output, a reduction of cerebral blood flow, a reduction in jugular flow, a reduction in jugular diameter, or an increase cervical impedance, among others.

In some examples, the physiological event detector circuit 210 may detect a postural change (e.g., from recumbent or sitting to upright posture) or a posture pattern (e.g., a sustained upright posture) that is more predictive of an onset of a future syncopal or presyncopal event. One or more posture parameters may be extracted from the posture signal, and used for recognizing the precipitating events associated with syncope onset with less false positive detections. Examples of the posture parameters may include change or posture patterns may speed of change from recumbent to sitting to upright, speed of change from sitting to upright, depth of angle of bend prior to upright (e.g., tying shoes and then standing), or length of duration of bend (e.g., picking up an object from the floor), among others. One or more of these posture parameters may be compared to their respective threshold values to distinguish a postural change, a posture pattern associated with syncope onset from a posture change, or a posture pattern associated with normal daily activity not predictive of an onset of syncope or presyncope. In an example, the physiological event detector circuit 210 may detect distinct patterns of posture change more likely associated with a syncope onset. In an example, a posture pattern of "sit to stand to sit" sequence may be detected, which may indicate patient's response to light-headedness or pre-syncopal event. In another example, the physiological event detector circuit 210 may detect sustained upright posture, such as for a duration of approximately 15 minutes to 30 minutes. In another example, the physiological event detector circuit 210 may detect a posture pattern following a sustained upright posture. Physical activities subsequent to sustained standing may have distinct patterns between syncopal patients and those free of syncope or presyncope. In one example, if the physiological event detector circuit 210 detects a quick sitting posture following sustained standing, then a precipitating event associated with syncope onset is detected. In another example, if the physiological event detector circuit 210 detects low-intensity and repetitive physical activities, then it is more likely a normal post-standing activity rather than a precipitating event associated with syncope onset. The low-intensity and repetitive physical activities may be a result of twitching, shifting weight from one side to another, or other normal activities to stimulate venous return. Other examples of physiological events that may be detected by the physiological event detector circuit 210 and predictive of an onset of a future syncopal or presyncopal event may include swallow activity, activities involving deep breath and bearing down (e.g., urination, defecation, coughing too hard and long), respiratory hyperventilation (such as due to anxiety or fear), dehydration, diuretics, or sleep pattern or sleep quality, among others.

The hemodynamic sensor circuit 220 may be configured to sense a hemodynamic signal from the patient via a second sensor 202, such as implantable, wearable, holdable, or otherwise an ambulatory sensor that directly or indirectly measures blood flow in the heart and the blood vessels. Examples of the hemodynamic sensor and the physiologic variables to sense may include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value or oxygen or carbon dioxide level in the blood or other tissues or organs in the body. In some examples, the hemodynamic signals sensed from a patient may be stored in a storage device, such as an electronic medical record (EMR) system. The hemodynamic sensor circuit 220 may receive the hemodynamic signal from the storage device.

The hemodynamic sensor circuit 220 may include a data acquisition circuit 222 that may be controllably triggered to initiate hemodynamic data acquisition upon an occurrence of a triggering event. As illustrated in FIG. 2, the control circuit 240 is coupled to the physiological event detector circuit 210 to trigger the data acquisition circuit 222 to acquire hemodynamic data in response to the detection of precipitating event. The precipitating event-triggered activation of hemodynamic sensing and data acquisition may provide several benefits. Because the precipitating event typically precedes a syncope onset, initiating hemodynamic data acquisition as early as the detection of the precipitating event may ensure capture of hemodynamic information prior to syncope onset. The syncope analyzer circuit 230 may use such pre-onset hemodynamic information to more precisely recognize the type of syncope. For example, pre-onset blood pressure drop and arrhythmia (such as bradycardia or sinus pause) may be evaluated and compared to each other to determine whether the syncope has a cardiac cause (e.g., arrhythmia), or caused by orthostatic hypotension where the blood pressure drop leads to both the arrhythmia and the syncope.

The precipitating event-triggered hemodynamic data acquisition may also be beneficial in reducing power consumption and optimizing device memory usage. Compared to sensors used for detecting the precipitating event (e.g., heart rate, ECG, or accelerometer for physical activities), activation and operation of hemodynamic sensors and hemodynamic data acquisition can be power- and memory-demanding. Syncope detection and classification may also require substantial amount of computing resource. The precipitating event-triggered activation of hemodynamic sensing and data acquisition, such as controlled by the controller circuit 240, may reduce the activation time of hemodynamic sensor operation, and thus conserve the device power and computing resources and thus reduces the operational cost.

The syncope analyzer circuit 230, coupled to the hemodynamic sensor circuit 220, may be configured to detect and classify a syncopal event. The detection and classification of syncope may be initiated in response to the detection of precipitating event, such as controlled by the control circuit 240. The hemodynamic data such as provided by the data acquisition circuit 222, and optionally the physiological signals used for detecting precipitating events, may be used for detecting and classifying the syncope.

The syncope analyzer circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The syncope analyzer circuit 230 may include circuit sets comprising one or more other circuits or sub-circuits, such as a syncope detector 232 for detecting a syncopal event, and a syncope classifier 234 for classifying the detected syncopal event into one of a plurality of syncope categories. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The syncope analyzer circuit 230 may be configured to generate a temporal profile of a hemodynamic parameter using the acquired hemodynamic data. The temporal profile may include an initial hemodynamic measurement within a first time window ($W_I$) subsequent to an onset of the precipitating event, and a late hemodynamic measurement within a second time window ($W_L$) subsequent to the first time window. The syncope detector 232 may detect a syncopal event, and the syncope classifier 234 may classify the detected syncopal event, using the temporal profile of the hemodynamic parameter. In an example, a metric of transition from the initial hemodynamic measurement to the late hemodynamic measurement may be used for detecting or classifying the syncope. The syncope classifier 234 may classify the syncope according to the underlying causes into a cardiogenic syncope, a non-cardiogenic syncope, a neurally mediated syncope, or an orthostatic syncope, among other syncope types. Alternatively or additionally, the syncope classifier 234 may classify the syncope according to severity of symptoms into no syncope, a presyncope, or a full-blown syncope, among other syncope stages of severity. Examples of the syncope detection and classification are discussed below, such as with reference to FIGS. 3-4.

The control circuit 240 may control the operations of the physiological event detector circuit 210, the hemodynamic sensor circuit 220, the syncope analyzer circuit 230, and the data and instruction flow between these system components. For example, as discussed above, the control circuit 240 may use the detected precipitating event to trigger hemodynamic data acquisition via the data acquisition circuit 222, or to trigger syncope detection and the classification via the syncope analyzer circuit 230. In some examples, the control circuit 240 may control the memory circuit 250 to store the hemodynamic data, such as acquired via the data acquisition circuit 222. In some examples, physiological signals used for detecting precipitating events may also be stored at the memory circuit 250. Data storage may be initiated in response to the detection of the precipitating event. The stored hemodynamic information and other physiological signals may be transmitted to an external device such as the external system 125 for clinician review and adjudication. The transmission may be initiated automatically at a specified time or periodicity, or via a data interrogation command via a programmer of the external system 125. In an example, upon the detection of the precipitating event, the control circuit 250 may flag a fiducial point in the hemodynamic data or other physiological signals stored in the memory circuit 250 for clinician review or offline syncope analysis. The pre-onset hemodynamic information, along with the flag of the precipitating event, may help clinician better recognize the causes or nature of the syncope.

In some examples, the control circuit 240 may use the detected precipitating event to trigger adjustment of one or more parameters for data acquisition or processing. The hemodynamic data or other physiological signals may be processed according to the adjusted parameters before being forwarded to the syncope analyzer circuit 230 for analysis (e.g., syncope detection and classification), or being stored in the memory circuit 250. In an example, the control circuit 240 may adjust a sampling rate for sampling the one or more hemodynamic signals or the physiological signals used for detecting precipitating events in response to the detection of the precipitating event. For example, the physiological event detector circuit 210 may perform continuous or periodic monitoring of ECG and blood pressure at respective sampling rates, and increase their respective sampling rates for ECG and blood pressure data acquisition upon the detection of the precipitating event. In another example, in response to the detection of the precipitating event, the control circuit 240 may adjust signal filter setting for filtering the hemodynamic signals or the physiological signals used for detecting precipitating events. The filter setting may include a low-pass frequency, a high-pass frequency, or a pass band gain, among other filter parameters. In another example, the control circuit 240 may selectively activate or deactivate data acquisition from one or more hemodynamic sensors in response to the detection of the precipitating event. For example, more hemodynamic sensors may be activated to acquire hemodynamic data upon the detection of the precipitating event. In some examples, the type of hemodynamic sensors activated for data acquisition may be dependent on the type of detected precipitating events. For example, if the precipitating events indicates a risk of future cardiogenic syncope, cardiac hemodynamic sensor may be activated. If the precipitating events indicates a risk of future neurally mediated syncope, PPG sensor or other hemodynamics sensors may be activated.

The user interface unit 260 may include an input unit and an output unit. In an example, at least a portion of the user interface unit 260 may be implemented in the external system 125. The input unit may receive user input for programming the physiological event detector circuit 210, the hemodynamic sensor circuit 220, and the syncope analyzer circuit 230, such as parameters and threshold values for detecting precipitating events, or for detecting and classifying syncope, among others. The input unit may include a keyboard, on-screen keyboard, mouse, trackball, touchpad, touch-screen, or other pointing or navigating devices. The output unit may include a display for displaying the patient physiological data, the detection of precipitating events, the hemodynamic data associated with the detected and classified syncope, or any intermediate measurements or computations, among others. The output unit 254 may include a printer for printing hard copies of signals and information related to syncope detection and classification. The signals and information may be presented in a table, a chart, a diagram, or any other types of textual, tabular, or graphical presentation formats. The presentation of the output information may include audio or other media format. In an example, the output unit 254 may generate alerts, alarms, emergency calls, or other forms of warnings to signal the system user about the detected medical events.

The optional therapy circuit 270 may be configured to deliver a therapy to the patient in response to the detection and classification of a syncopal event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 270 may modify an existing therapy, such as adjust a stimulation parameter or drug dosage.

Figure 3:
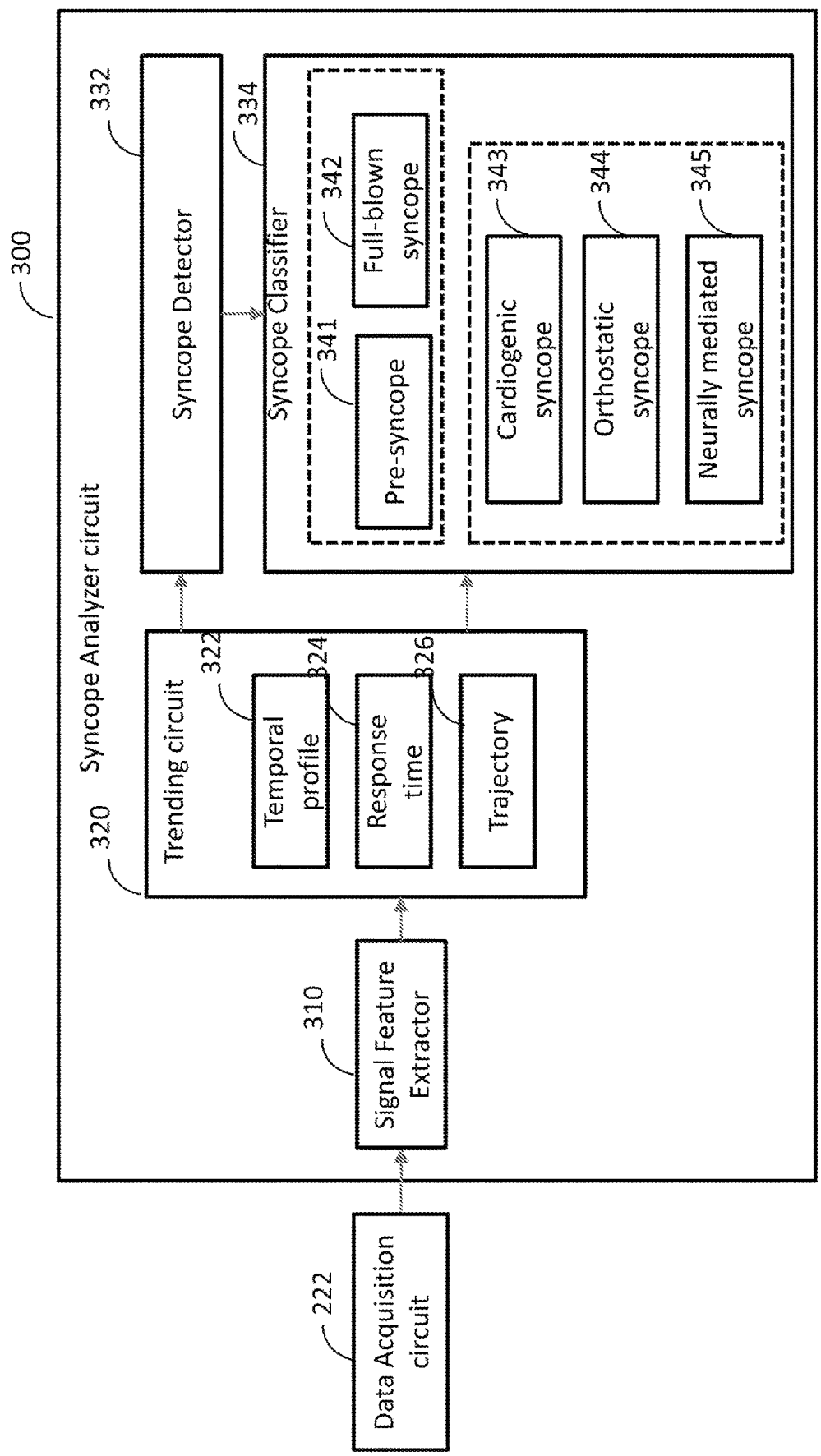
FIG. 3 illustrates generally an example of a syncope analyzer circuit for detecting and classifying a syncopal event.

FIG. 3 illustrates generally an example of a syncope analyzer circuit 300 configured to detect and classify a syncopal event. The syncope analyzer circuit 300, which is an embodiment of the syncope analyzer circuit 230 of the syncope monitor system 200, may include a signal feature extractor 310, a trending circuit 320, a syncope detector 332, and a syncope classifier 334. The signal feature extractor 310 may extract signal characteristics from the acquired hemodynamic data or optionally from the physiological signal used for detecting precipitating event. The extracted signal features may include statistical or morphological measurements from a hemodynamic signal or other physiological signal. The trending circuit 320 may trend the extracted signal feature over time, and generate one or more of temporal profile 322, response time 324, and trajectory 326 of the extracted signal feature. The temporal profile 322 represents temporal variation of the extracted signal feature subsequent to the precipitating event detection. In an example, the temporal profile 322 may include at least an initial measurement of the extract signal feature within a first time window ($W_I$) with respect to the precipitating event, and a late measure of the extracted signal feature within a second time window ($W_L$) subsequent to the first time window $W_I$. The first and second time windows may or may not overlap in time. The response time 324 represents transition time from the initial measurement to the late measurement of the extracted signal feature. The trajectory 326 may include at least one intermediate measurement of the extracted signal feature during a time period after the window $W_I$ but before the window $W_L$.

In an example, the hemodynamic sensor circuit 220 may be coupled to a heart sound sensor to sense a HS signal, and the data acquisition circuit 222 may acquire HS data in response to the detection of a precipitating event. The HS sensor may take the form of an accelerometer, an acoustic sensor, a microphone, a piezo-based sensor, or other vibrational or acoustic sensors. The accelerometer can be a two-axis or a three-axis accelerometer. Examples of the accelerometer may include flexible piezoelectric crystal (e.g., quartz) accelerometer or capacitive accelerometer, fabricated using micro electro-mechanical systems (MEMS) technology. The HS sensor may be included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various HS components.

The signal feature extractor 310 may detect one or more HS components from the received HS signal, which may include a first (S1) heart sound, a second (S2) heart sound, a third (S3) heart sound, or a fourth (S4) heart sound. S1 is associated with the vibrational sound made by the heart during tensing of the mitral valve. S2 is produced by the closure of the aortic and pulmonary valves, and marks the beginning of diastole. The signal feature extractor 310 may generate one or more HS metrics using the detected HS components. In an example, the HS metrics may include a S1 intensity and a S2 intensity. The S1 intensity may be measured as a signal amplitude or signal power during a S1 window. The S2 intensity may be similarly measured as a signal amplitude or signal power during a S2 window. The S1 window or S2 window may be defined by a user. In an example, the S1 window may begin at 50 milliseconds (msec) following an R wave (or a localized ventricular depolarization) and have a duration of 300 msec. The S2 window may begin at specified offset following a detected R wave (or a localized ventricular depolarization) or S1 heart sound. The S1 window or S2 window may also be determined based on heart rate.

The HS metrics may include one or more HS-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. The HS-based cardiac timing intervals may be correlated to cardiac performance or hemodynamic status. For example, STI may be correlated to cardiac contractility and can be used to monitor hemodynamic profile and to detect and evaluate syncope.

The trending circuit 320 may trend one or more HS metrics, such as S1 intensity or S2 intensity or HS-based cardiac timing intervals, and generate one or more of HS temporal profiles. In an example, S1 intensity is correlated to cardiac contractility, and S2 intensity is correlated to blood pressure. A temporal profile of S1 intensity or a temporal profile of S2 intensity may therefore represent cardiac and hemodynamic responses following the precipitating event. Additionally or alternatively, the trending circuit 320 may generate response time 324 representing time elapsed from an initial HS response during the window $W_I$ to the late HS response during the window $W_L$, or a HS trajectory including one or more intermediate measurements of HS metrics between the windows $W_I$ and $W_L$.

In another example, the hemodynamic sensor circuit 220 may be coupled to an optoelectronic sensor configured to sense a photoplethysmogram (PPG) signal, and the data acquisition circuit 222 may acquire PPG data in response to the detection of a precipitating event. The optoelectronic sensor comprises an infrared emitter and a photo diode detector to detect changes in optical (e.g., infrared) reflectance resulting from varying blood flow. The optoelectronic sensor may be placed on the skin, such as in proximity to capillaries, such that the reflectance of the infrared light from the emitter to the detector may change in accordance to capillary blood volume. The signal feature extractor 310 may extract one or more PPG parameters from the PPG signal, including a heart rate and a measurement of oxygenation saturation level of arterial blood ($SpO_2$). The $SpO_2$ may be determined by measuring the absorption at two different wavelengths. In an example, the data acquisition circuit 222 may record a PPG waveform containing temporal changes of $SpO_2$ level. The signal feature extractor 310 may extract from the PPG waveform one or more statistical or morphological features. Examples of the PPG parameters may include a change in peak amplitude of a PPG pulse, a change in area under the curve of a PPG pulse, or a change in timing of PPG pulse with respect to a reference time, among other parameters. The trending circuit 320 may trend one or more of the PPG parameters and generate accordingly one or more of temporal profiles, response time, or trajectory of the one or more PPG parameters.

The syncope detector 332, which is an embodiment of the syncope detector 232, may detect a syncopal event using one or of the trended signal features, such as the temporal profile 322, the response time 324, or trajectory 326 of a HS component or a PPG parameter, as previously discussed with reference to FIG. 2. In an example, the syncope detector 332 may detect a syncope if the S1 temporal profile or the S2 temporal profile does not show substantial recovery within a specified time period following the precipitating event. The recovery HS temporal profile may be based on a comparison of a HS metric, such as S1 intensity of S2 intensity, measured during the window $W_L$ to the corresponding HS metric measured during the window $W_I$. A syncope is detected if the late S1 intensity (or S2 intensity) fails to increase from the early S1 intensity (or S2 intensity) level by an amount exceeding an intensity threshold, indicating insufficient hemodynamic recovery. Additionally or alternatively, a syncope is detected if the time elapsed for the late S1 intensity (or S2 intensity) to recover to a specified level exceeds a time threshold, indicating no recovery or substantially slow hemodynamic recovery. Additionally or alternatively, a syncope is detected if the trajectory of the S1 intensity (or the trajectory S2 intensity) from the first window $W_I$ to the second window $W_L$ fails to follow an expected recovery pattern within a specific margin, suggesting irregular or insufficient hemodynamic recovery. The syncope detector 332 may alternatively use one or more of the temporal profile, the response time, or the trajectory of a PPG parameter to detect the syncope, in a similar fashion to the detection based on HS parameters. In some examples, the syncope detector 332 may further use information from patient medical history, such as pre-syncopal events that patient experiences in the past, to detect syncope. In an example, the syncope detector 332 may adjust a detection parameter to have a higher sensitivity to syncopal (e.g., by lowering a detection threshold) if the patient has a history of frequent pre-syncope. In some examples, contextual information such as time of day, or ambient conditions such as environmental temperature or air pressure may also be used to detect syncope.

The syncope classifier 334, which may be an embodiment of the syncope classifier 234, may be configured to classify a syncope, such as the one detected by the syncope detector 332, into one of a plurality of syncope categories. The syncope classification may be based on significance of hemodynamic impact and symptoms, such as pre-syncope 341 or full-blown syncope 342, or based on causes or triggering mechanisms of syncope, such as one of a cardiogenic syncope 343, an orthostatic syncope 344, or a neurally mediated syncope 345, among other syncope types. The presyncope 341 is a prodromal state before full development of signs and symptoms of full-blown syncope 342. Presyncope may be characterized by lightheadedness and a presented feeling of faintness but persevered consciousness, compared to the full-blown syncope 342, which typically results in actual fainting and a loss of consciousness. In some examples, the syncope detector 332 may detect a potential syncopal event, and the syncope classifier 334 may accept or reject the syncope detection. For example, the syncope classifier 334 may generate a "no syncope" classification.

The syncope classifier 334 may classify the syncope using a trended feature, such as one or more of the temporal profile 322, the response time 324, or the trajectory 326 of a feature extracted from the hemodynamic signal or other physiological signals. In an example, the syncope classifier 334 may use temporal profiles of one or more HS metrics to classify the syncope. For example, although both pre-syncope 341 and the full-blown syncope 342 may be characterized by an initial sudden blood pressure drop, pre-syncope 341 may have a relatively smaller initial blood pressure drop in response to the precipitating event, followed by a relatively quicker blood pressure recovery. As previously discussed, S2 intensity may be correlated to the blood pressure, and S2 temporal profile may represent hemodynamic recovery following the precipitating event. The syncope classifier 334 may classify the syncope as a presyncope 341 if the S2 temporal profile satisfies a specified condition, such as when the initial S2 intensity during the first window $W_I$ exceeds a threshold (indicating moderate initial blood pressure drop), or when the late S2 intensity during the second window $W_L$ recovers from the early S1 intensity by an amount exceeding an intensity threshold within a specified time (indicating substantial and relatively timely recovery of blood pressure). In another example, the cardiogenic syncope 343 may typically be accompanied by irregular heartbeats or cardiac arrhythmias, which may cause sudden change in cardiac contractility or atrial-ventricular synchrony. As previously discussed, S1 intensity is generally correlated to the cardiac contractility. The syncope classifier 334 may discriminate cardiogenic syncope from non-cardiogenic syncope based on the detection of arrhythmia or insufficient recovery of S1 temporal profile indicating a deterioration of contractility. In another example, the syncope classifier 334 may discriminate cardiogenic syncope from non-cardiogenic syncope based on temporal relationship between a change in blood pressure and an arrhythmia onset. Cardiogenic syncope may be characterized by an arrhythmia preceding blood pressure drop, and non-cardiogenic syncope may be characterized by a blood pressure drop preceding an arrhythmia onset. In some examples, the syncope classifier 334 may further classify the non-cardiogenic syncope into orthostatic syncope 344 or neurally mediated syncope 345, using the one or more of the temporal profile 322, response time 324, or trajectory 326 of one or more of S1 intensity or S2 intensity, as to be discussed as follows with reference to FIG. 4.

Figure 4A:
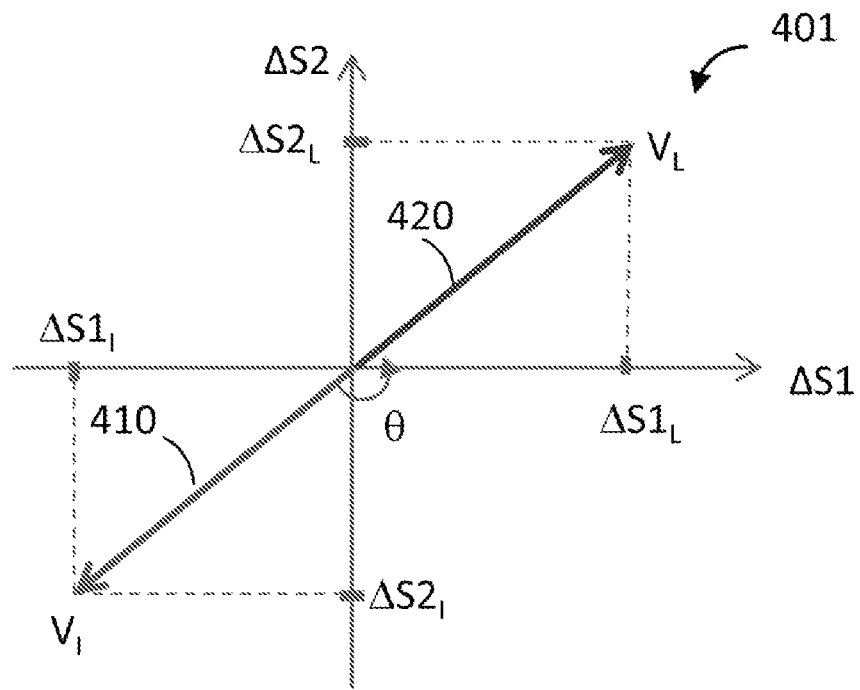
FIGS. 4A-C illustrate generally graphs of heart sound (HS) vectors to represent HS response profile following a precipitating event.
Figure 4B:
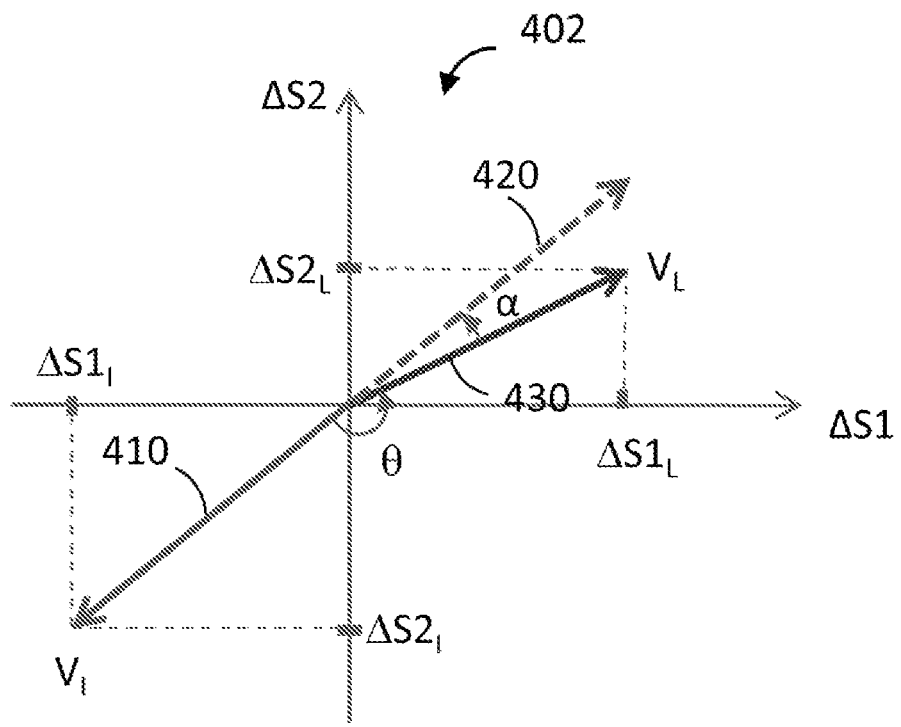
Figure 4C:
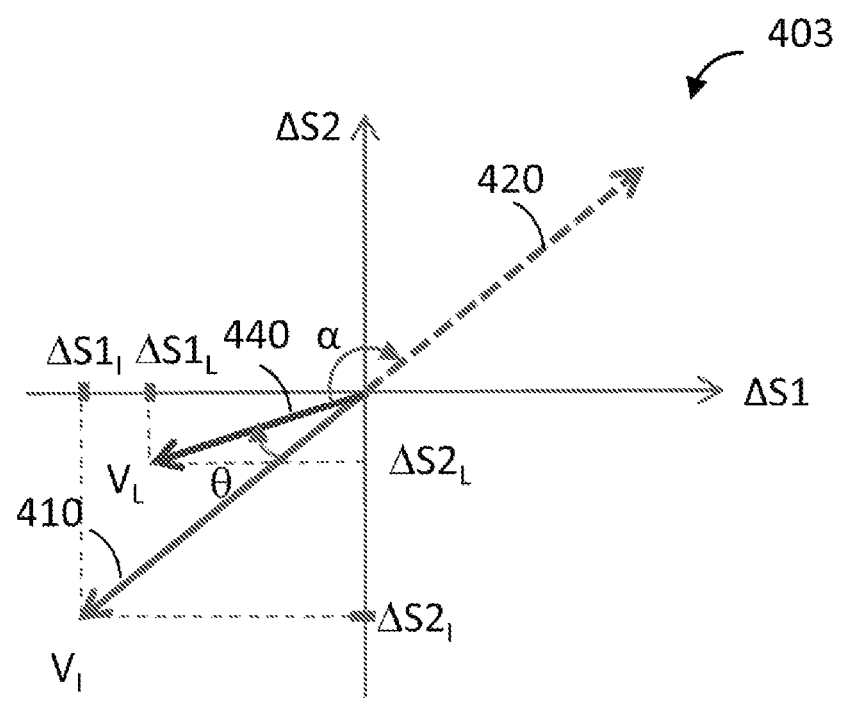

FIGS. 4A-C illustrate generally graphs of heart sound (HS) vectors in a vector space representing HS responses following a precipitating event, such as one detected by the physiological event detector circuit 210. In these examples, the HS response is represented by an initial HS vector $V_I$, and a late HS vector $V_L$. The initial and late HS vectors each comprise two components: a S1 intensity change ($\Delta S1$) and a S2 intensity change ($\Delta S2$). As such, each HS vector is plotted in a vector space spanned by $\Delta S1$ (in the horizontal axis) and $\Delta S2$ (in the vertical axis). The HS intensity change such as $\Delta S1$ and $\Delta S2$, and the HS vectors such as $V_I$ and $V_L$, may be generated using the syncope analyzer circuit 300.

The initial HS vector $V_I$ may represent hemodynamic status change during an acute phase (e.g., during $W_I$) following the precipitating event. $V_I$ may comprise an initial S1 intensity change $\Delta S1_I$ and an initial S2 intensity change $\Delta S2_I$, denoted by $V_I=(\Delta S1_I, \Delta S2_I)$. $\Delta S1_I$ is a change from a baseline S1 intensity measurement ($S1_0$) to an initial S1 intensity measurement ($S1_I$) post precipitating event, and $\Delta S2_I$ indicates a change from a baseline S2 intensity measurement ($S2_0$) to an initial S2 intensity measurement ($S2_I$) post precipitating event. The baseline HS measurements, $S1_0$ and $S2_0$, may be respectively computed as mean, median, mode, or other central tendency of multiple measurements of S1 intensity or S2 intensity at multiple cardiac cycles during a time period prior to the detection of a precipitating event, such as a time period when the patient is known to be syncope-free or hemodynamically stable. The time period for establishing the $S1_0$ and $S2_0$ may include at least a portion of the time period of the detected precipitating event, such as during an onset of a cardiac arrhythmia, or during a postural transition to an upright posture. The initial HS measurements, $S1_I$ and $S2_I$, may be respectively computed as mean, median, mode, or other central tendency of multiple measurements of S1 intensity or S2 intensity at multiple cardiac cycles within the first time window $W_I$. In an example, $W_I$ is approximately 3-5 seconds following the detection of precipitating event. The baseline HS measurements and the initial HS measurements may be generated using the trending circuit 320.

The late HS vector $V_L$ may represent delayed hemodynamic response following the acute hemodynamic response. $V_L$ may comprise a late S1 change $\Delta S1_L$ and a late S2 change $\Delta S2_L$, denoted by $V_L=(\Delta S1_L, \Delta S2_L)$. $\Delta S1_L$ is a change from the initial S1 intensity measurement ($S1_I$) to a late S1 intensity measurement ($S1_L$), and $\Delta S2_L$ indicates a change from the initial S2 intensity measurement ($S2_I$) to a late S2 intensity measurement ($S2_L$). The late HS measurements, $S1_L$ and $S2_L$, may be respectively computed as mean, median, mode, or other central tendency of multiple measurements of S1 intensity or S2 intensity at multiple cardiac cycles within the second time window $W_L$. In an example, $W_L$ is approximately 10-20 seconds after the end of the first time window $W_I$. In another example, $W_L$ is approximately 30 seconds to three minutes after the end of $W_I$. In yet another example, WL is up to approximately 45 minutes after the end of $W_I$. The late HS measurements, $S1_L$ and $S2_L$, may be generated using the trending circuit 320.

The initial HS vector $V_I$ and the late HS vector $V_L$ may be used to characterize a transition from the acute phase to a later recovery phase of patient hemodynamic response. The trending circuit 320 may generate one or more parameters, such as the temporal profile 322, the response time 324, or the trajectory 326 to quantify the transition from $V_I$ and $V_L$, optionally along with other information such as one or more intermediate HS vectors between $V_I$ and $V_L$. The syncope detector 332 may detect, and the syncope classifier 334 may classify, the syncope using one or more quantifiers of the transition from $V_I$ and $V_L$.

Graph 401 in FIG. 4A illustrates $V_I$ and $V_L$ in a syncope-free scenario with complete hemodynamic recovery. In response to the precipitating event, and during the acute phase within $W_I$, both the venous return to heart and the strove volume decrease, resulting in a fainter S1 than baseline S1 level ($S1_I<S1_0$). The initial phase is also characterized by a sudden drop in blood pressure from baseline blood pressure level, resulting in initial drop in S2 intensity ($S2_I<S2_0$). As both $\Delta S1_I$ and $\Delta S2_I$ are negative, the initial HS vector $V_I$ 410 is at the third quadrant of the $\Delta S1$-$\Delta S2$ vector space. During the subsequent recovery phase within $W_L$, the initial drop in blood pressure may unload the baroreflex receptors. This may reflectively stimulate the sympathetic nerve and suppress the parasympathetic nerve activity, causing a series of cardiovascular responses including vasoconstriction, increased cardiac contractility, and faster heart rate. Consequently, blood pressure increases and hemodynamic stability may be restored. Corresponding to the hemodynamic recovery, both the late S1 intensity ($S1_L$) and the late S2 intensity ($S2_L$) increase substantially from their respective initial drop states ($S1_I$ and $S2_I$, respectively), that is, $S1_L>S1_I$ and $S2_L>S2_I$. As such, both the late S1 intensity change $\Delta S1_L$ and late S2 intensity change $\Delta S2_L$ take positive values; and the late HS vector $V_L$ 420 is at the first quadrant of the $\Delta S1$-$\Delta S2$ vector space. When the recovery of S1 intensity and S2 intensity reaches their respective baseline levels, a transition angle $\theta$ between the early HS vector $V_I$ 410 and the late vector $V_L$ 420 is approximately 180 degrees, indicating a full restoration of hemodynamics. In an example, the trending circuit 320 may compute the temporal profile 322 using the transition angle $\theta$. The syncope detector 332 may detect an onset of syncope or presyncope if $\theta$ falls outside a specified range, such as 180 degrees with a specific tolerance margin. In an example, the S1 intensity change (horizontal axis) may be normalized with respect to the absolute value of initial S1 intensity change $\Delta S1_I$. Similarly, the S2 intensity change (vertical axis) may be normalized with respect to the absolute value of initial S2 intensity change $\Delta S2_I$. As such, the normalized $\Delta S1_I$ and the normalized $\Delta S2_I$ have the same value of negative one, and the initial HS vector $V_I$ is approximately 135 degrees.

Graph 402 in FIG. 4B illustrates $V_I$ and $V_L$ during an orthostatic syncope. Following the concurrent S1 intensity drop and S2 intensity drop during the acute phase as represented by the initial HS vector $V_I$, the initial drop in blood pressure may unload the baroreflex receptors. However, in certain old patients or those with chronic heart disease, the reduced baroreflex sensitivity may negatively affect the autonomic response to initial blood pressure drop. As a result, although cardiovascular responses such as vasoconstriction, increased cardiac contractility, and faster heart rate are present during the recovery phase within $W_L$, the blood pressure may not able to restore adequately. This physiological response may be represented by a substantial increase in late S1 intensity ($S1_L$) from its initial drop state ($S1_I$) (corresponding to sufficient recovery of contractility and increase in heart rate), accompanied by inadequate increase in late S2 intensity ($S2_L$) from its initial drop states ($S2_I$). In an example, the S1 intensity may reach its baseline level $S1_0$, but S2 intensity may not reach its baseline level $S2_0$. The transition angle $\theta$ between the early HS vector $V_I$ 410 and the late vector $V_L$ 420 is greater than 90 degrees and less than 180 degrees. For comparison, FIG. 4B also shows the HS response vector 420 as an ideal late HS response with complete hemodynamic recovery. The angle ($\alpha$) between the HS response vector $V_L$ 430 and the ideal HS response may be used to quantify the inadequacy of blood pressure recovery. The syncope detector 332 may classify the detected syncope as orthostatic syncope if the angle $\theta$ falls within a specified range, such as between 90 and 180 degrees, or between 135 to 180 degrees (i.e., both $\Delta S1_L$ and $\Delta S2_L$ take positive values). Alternatively, the syncope detector 332 may classify the detected syncope as orthostatic syncope if the angle $\alpha$ falls in a specified range such as between 0 and 90 degrees.

Graph 403 in FIG. 4C illustrates $V_I$ and $V_L$ during a neurally mediated syncope, such as a vasovagal syncope. Following the concurrent S1intensity drop and S2 intensity drop during the acute phase as represented by the initial HS vector $V_I$, the initial drop in blood pressure may activate a mechanoreceptor-mediated Bezold-Jarisch reflex. Vagal afferents carry signals to higher central nervous system centers, which act through autonomic nuclei in the medulla to cause a massive stimulation of the parasympathetic system and abolition of sympathetic tone, causing hypotension and bradycardia, and elicit vasovagal syncope. The autonomic response to the activation of Bezold-Jarisch reflex reflectively stimulate vasodilation (as opposed to vasoconstriction in case of orthostatic syncope), further reduce cardiac contractility, and further decrease the heart rate, causing bradycardia. Accordingly, the late S1 intensity (S L) may further decrease from its initial drop state ($S1_L<S1_I$) (which corresponds to further deterioration in contractility and bradycardia). At the same time, the blood pressure may also continue decreasing from the initial sudden drop, resulting in a late S2 intensity ($S2_L$) further decreasing from its initial drop state ($S2_L<S2_I$). As such, both the late S1 intensity change $\Delta S1_L$ and late S2 intensity change $\Delta S2_L$ take negative values; and the late HS vector $V_L$ 440 is at the third quadrant of the $\Delta S1$-$\Delta S2$ vector space. The transition angle $\theta$ between the early HS vector $V_I$ 410 and the late vector $V_L$ 440 is less than 90 degrees. The angle ($\alpha$) between the HS response vector $V_L$ 440 and the ideal HS response (corresponding to HS response vector $V_L$ 430) is greater than 90 degrees, representing greater deviation of the late HS response from the expected HS response. The syncope detector 332 may classify the detected syncope as neurally mediated syncope if $\theta$ falls within a specified range, such as between 0 and 90 degrees, or alternatively if the angle $\alpha$ falls in a specified range such as between 90 and 180 degrees.

Although in FIGS. 4A-C the hemodynamic responses during the acute phase and the recovery phase are each represented by a two-dimensional HS response vector comprising measurements of S1 intensity change and S2 intensity change, this is only meant by way of example but not limitation. Other hemodynamic parameters may similarly be used in lieu of one or both of S1 intensity or S2 intensity, or in addition to S1 intensity and S2 intensity. In an example, heart rate (HR) may be trended, and a HR temporal profile in response to detection the precipitating event may be used to detect or classify a syncopal event. For example, a hemodynamic vector space may be spanned by a heart rate change ($\Delta HR$) and $\Delta S2$. A composite hemodynamic status change may be represented by a transition from an initial hemodynamic vector $V_I$ comprising $\Delta HR_I$ and $\Delta S2_I$, to a late hemodynamic vector $V_L$ comprising $\Delta HR_L$ and $\Delta S2_L$. In another example, the hemodynamic vector space may be a three-dimensional space spanned by $\Delta HR$, $\Delta S1$, and $\Delta S2$. A composite hemodynamic status change may be represented by a transition from an initial hemodynamic vector $V_I=(\Delta HR_I, \Delta S1_I, \Delta S2_I)$ to a late hemodynamic vector $V_L$ comprising $V_L=(\Delta HR_L, \Delta S1_L, \Delta S2_L)$. In another example, the PPG parameters may be extracted from a signal acquired by a PPG sensor, and initial hemodynamic response vectors and late hemodynamic response vectors based on PPG parameters may similarly be defined and used to detect occurrence of syncope, or to discriminate one syncope type from another, such as between orthostatic syncope and the neurally mediate syncope.

In some examples, the hemodynamic response may be represented by a single hemodynamic parameter, such as $\Delta S1$ or $\Delta S2$, or another hemodynamic parameter, as opposed to the two-dimensional HS response vector $(\Delta S1, \Delta S2)$ as discussed above. The initial HS vector $V_I$ and the late HS vector $V_L$ may be respectively represented by $\Delta S1_I$ and $\Delta S1_L$, or respectively represented by $\Delta S2_I$ and $\Delta S2_L$. Such HS vectors represent the hemodynamic status changes in a one-dimensional vector space.

In some examples, the initial HS response vector may be represented by the measurement of HS parameter (such as S1 intensity or S2 intensity) during the acute phase within the window $W_I$, as opposed to a change from the corresponding baseline HS intensity measurements. Similarly, the late HS response vector may be represented by the measurement of HS parameter, such as S1 intensity or S2 intensity during the recovery phase within the window $W_L$, as opposed to a change from the corresponding initial HS intensity measurement within the window $W_I$. A transition from the initial HS intensity measurement to a late HS intensity measurement may be used to detect and classify the syncope.

Figure 5:
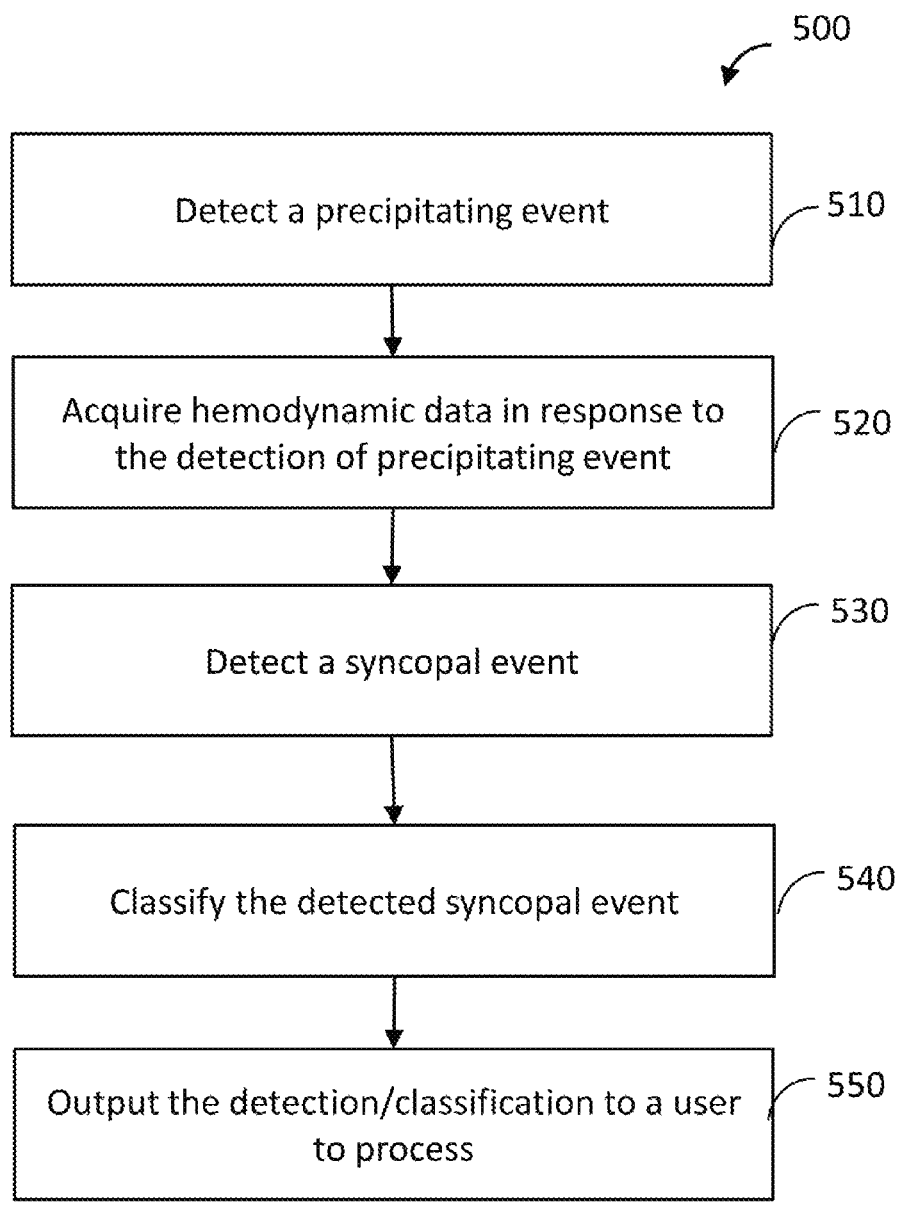
FIG. 5 illustrates generally an example of a method for monitoring a patient for syncope.

FIG. 5 illustrates generally an example of a method 500 for monitoring a patient for syncope. The method 500 may be implemented and executed in an ambulatory medical device such as an implantable or wearable medical device, or in a remote patient management system. In an example, the method 500 may be implemented in and executed by the AMD 110, one or more devices in the external system 125, the syncope monitor system 200 or a variation thereof.

The method 500 begins at 510, where a precipitating event may be detected from one or more physiological signals sensed from the patient. The precipitating event may include an event associated with an onset of a future syncopal or a presyncopal event. Examples of the physiological signals used for detecting the precipitating event may include surface electrocardiography (ECG), subcutaneous ECG, intracardiac electrogram (EGM), heart rate signal, physical activity signal, posture signal, a thoracic or cardiac impedance signal, or a blood pressure signal, among others. The type of precipitating event may be specified by a user. The precipitating event may be based on patient medical history, such as chronic heart diseases, neurological diseases, or information about prior syncopal or presyncopal episodes. In an example, if a patient has a history of particular type of syncope (e.g., cardiogenic, orthostatic, or neurally mediated syncope), or if the patient is identified as having a high risk of a particular type of syncope, then at 510 one or more precipitating events corresponding to the identified syncope type may be detected. The correspondence between the syncope type and the precipitating events may be established using patient population data. Examples of methods for detecting the precipitating events are discussed below, such as with reference to FIG. 6.

At 520, hemodynamic data may be acquired in response to the detection of precipitating event. The hemodynamic data may be sensed using an implantable, a wearable, a holdable, or otherwise ambulatory hemodynamic sensors that directly or indirectly measures dynamics of the blood flow in the heart chambers or in the blood vessels. Examples of the hemodynamic sensor and the physiologic variables to sense may include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value or oxygen or carbon dioxide level in the blood or other tissues or organs in the body. Compared to the sensors used for sensing physiological signals and detecting precipitating events (e.g., heart rate, ECG, or accelerometer for posture and physical activities), activation and operation of hemodynamic sensors and hemodynamic data acquisition may be more power- and memory-demanding. The precipitating event-triggered activation of hemodynamic data acquisition may conserve the device power and improve efficient usage of device memory and computing resources.

In some examples, one or more parameters for data acquisition or processing may be adjusted in response to the detection of the precipitating event. Examples of such parameters may include a sampling rate for sampling the one or more hemodynamic signals or the physiological signals used for detecting precipitating events, or a signal filter setting for filtering the hemodynamic signals or the physiological signals used for detecting precipitating events. The filter setting may include a low-pass frequency, a high-pass frequency, or a pass band gain, among other filter parameters. In some examples, one or more hemodynamic sensors may be selectively activated or deactivated for acquiring sensor data in response to the detection of the precipitating event.

At 530, a syncope can be detected such as by using the syncope detector circuit 232 or 332. The hemodynamic data acquired in response to the detection of a precipitating event, and optionally the physiological signals used for detecting precipitating events, may be used to detect syncope. In an example, a temporal profile of a hemodynamic parameter may be generated using the acquired hemodynamic data. The temporal profile of the hemodynamic parameter may include an initial hemodynamic parameter measurement within a first time window subsequent to an onset of the precipitating event, and a late hemodynamic parameter measurement within a second time window subsequent to the first time window. The initial hemodynamic parameter measurement may represent an acute phase hemodynamic response, and the late hemodynamic parameter measurement may represent hemodynamic recovery after the acute phase of response. In an example, the first time window may be approximately 3-5 seconds following the onset of the precipitating event, and the second time window may be approximately 10-20 seconds following the termination of the first time window.

The detection of the syncopal event may be based on the temporal profile of the hemodynamic parameter. In an example, a syncopal event is detected if the late hemodynamic parameter measurement fails to increase from the early hemodynamic parameter measurement by an amount that exceeds a specified threshold, indicating insufficient hemodynamic recovery. In some examples, a response time, which may be measured as time elapsed from the initial hemodynamic parameter measurement to the late hemodynamic parameter measurement may additionally or alternatively be used for detecting syncope. A syncopal event is detected if the response time exceeds a time threshold, indicating no recovery or substantially slow hemodynamic recovery. In some examples, the syncope detection may be based on a trajectory of hemodynamic parameter. The trajectory may include hemodynamic parameter measurements at different time following the precipitating events. In an example, the trajectory may include one or more intermediate measurements between the initial hemodynamic parameter measurement and the late hemodynamic parameter measurement. A syncopal event is detected if the trajectory of fails to follow an expected recovery pattern within a specific margin, suggesting irregular or insufficient hemodynamic recovery.

At 540, the detected syncopal event may be classified into one of a plurality of syncope categories, such as by using the syncope classifier circuit 234 or 334. Hemodynamic data acquired in response to the detection of a precipitating event, and optionally the physiological signals used for detecting precipitating events, may be used for syncope classification. The syncope classification may be based on severity of hemodynamic compromise or patient signs and symptoms. The syncope classification may also be based on causes or triggering mechanisms of syncope. In an example, a detected syncopal event may be classified as one or more of a presyncope, a full-blown syncope, a cardiogenic syncope, a non-cardiogenic syncope, an orthostatic syncope, a neurally mediated syncope, among other syncope types. In some examples, a potential syncope detected at 530 may be rejected at 540, resulting in a "no syncope" classification. One or more of the temporal profile, the response time, or the trajectory of a hemodynamic parameter may be used for syncope classification, as previously discussed with reference to the syncope classifier 334 in FIG. 3.

At 550, the detection and classification of a syncope may be output to a user or a process. This may include displaying the patient physiological data, the detection of precipitating events, the hemodynamic data associated with the detected and classified syncope, or any intermediate measurements or computations, among others. In some examples, the hemodynamic information and other physiological signals associated with the detection or classification of syncope may be transmitted to an external device for clinician review, adjudication, or other offline syncope analysis. In some examples, a therapy may be delivered to the patient in response to the detection and classification of a syncopal event. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified in response to the detection or classification of a syncope, such as adjust a stimulation parameter or drug dosage.

Figure 6:
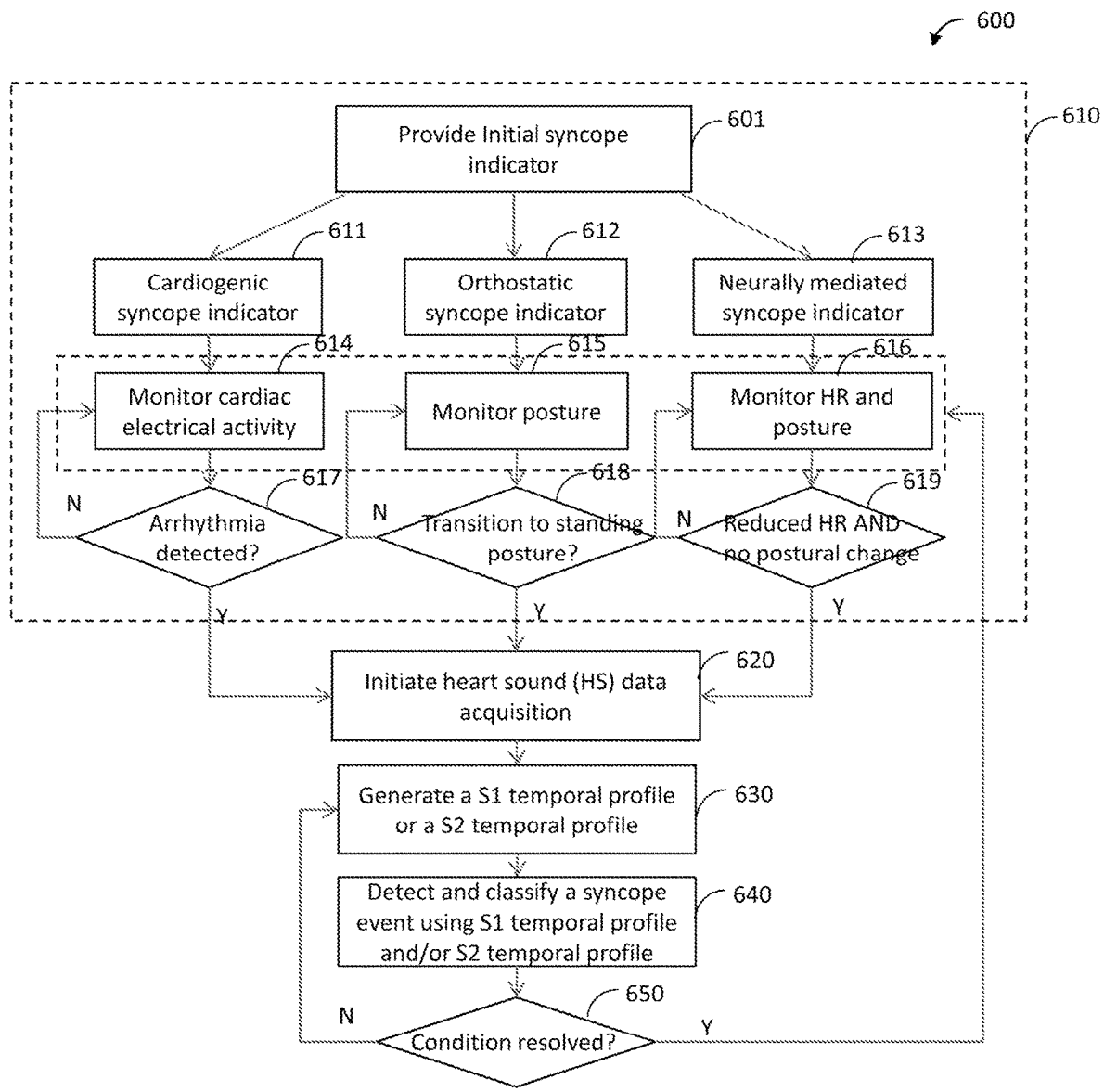
FIG. 6 illustrates generally an example of a method using HS for detecting and classifying a syncopal event.

FIG. 6 illustrates generally an example of a method 600 for detecting and classifying a syncopal event using heart sounds. The method 600 may be an embodiment of the method 500, and may similarly be implemented and executed in an ambulatory medical device or in a remote patient management system.

The method 600 begins at 610 to detect a precipitating event based on information about patient medical history. As illustrated in FIG. 6, the detection of precipitating event may begin at 601 by providing an initial syncope indicator of the patient. The initial syncope indicator indicates a patient risk of experiencing a particular type of syncopal event based on patient health condition, medical history, risk factors such as determined from patient population date. For example, if a patient has a history of particular type of syncope (e.g., cardiogenic, orthostatic, or neurally mediated syncope), then an initial syncope indicator may be determined to indicate patient high risk of developing a future syncope of the same type. By way of example and not limitation, FIG. 6 illustrate patient indicators including cardiogenic syncope indicator 611, orthostatic syncope indicator 612, and neurally mediated syncope indicator 613.

Certain precipitating events corresponding to the patient syncope indications may be detected. The correspondence between the syncope type and the precipitating events to be detected may be established using patient population data. For example, if the patient is identified to have a risk of cardiogenic syncope at 611, then at 614, cardiac electrical activities, such as ECGs or cardiac EGMs may be monitored to detect a cardiac arrhythmia. A cardiac arrhythmia may be a precipitating factor leading to a cardiogenic syncopal event. The cardiac arrhythmia may include a bradycardia, a tachycardia, or a sinus pause or asystole, among others. The cardiac arrhythmia may be detected using heart rate, heart rate stability, cardiac signal waveform morphology, or other signal characteristics derived from the cardiac electrical activity signal. If a cardiac arrhythmia is detected, the arrhythmia detection may trigger acquisition of hemodynamic data at 620; otherwise, the monitoring of the cardiac electrical activity may be continued at 614.

If at 612 the patient is indicated to have a risk of orthostatic syncope, then patient posture may be monitored at 615 for any posture related event precipitating orthostatic hypotension that may lead to syncope. The posture may be detected using a posture sensor such as an accelerometer, a tilt switch, or a thoracic impedance sensor for sensing a change in thoracic impedance correlated to posture change. A sudden transition to an upright posture may produce gravitational pooling of blood in lower extremities. Patients with blunted baroreflex sensitivity may have inadequate autonomic response to help restore blood pressure adequately within a short time following the postural change. If at 618 a sudden transition to an upright posture is detected, the acquisition of hemodynamic data may be initiated at 620; otherwise, the monitoring of the posture may be continued at 615.

If the patient is indicated to have a neurally mediated syncope at 613, then both the heart rate (HR) and the posture may be monitored at 616. Neurally mediated syncope, such as vasovagal syncope, may be attributed to malfunction in the parts of the nervous system that regulate heart rate and blood pressure. A substantial reduction of heart rate such as falling below a heart rate threshold of approximately 40 bpm with no concomitant postural change are precipitating events of vasovagal syncope. In another example, vasovagal syncope may also be triggered by prolonged standing or upright sitting and lack of physical activity. Detection of such precipitating events at 619 may trigger the acquisition of hemodynamic data at 620. If the precipitating event is not detected, monitoring of the heart rate and posture, or optionally physical activity, may be resumed at 616.

In some examples, the posture sensing and analysis at one or more of steps 615, 616, 615, or 616 may include identifying a postural change or a posture pattern that is likely to be associated with syncope onset. One or more posture parameters may be extracted from the posture signal, and used for recognizing the precipitating events associated with syncope onset with less false positive detections. Examples of the posture parameters may include change or posture patterns may speed of change from recumbent to sitting to upright, speed of change from sitting to upright, depth of angle of bend prior to upright (e.g., tying shoes and then standing), or length of duration of bend (e.g., picking up an object from the floor), among others. One or more of these posture parameters may be compared to their respective threshold values to distinguish a postural change or a posture pattern associated with syncope onset from a posture change or pattern associated with normal daily activity not predictive of an onset of syncope or presyncope.

At 620, hemodynamic data may be acquired in response to the detection of a precipitating event, such as an arrhythmia, a transition to standing posture, a reduced heart arte accompanied by no substantial posture change, or a sustained standing posture with physical inactivity, as discussed above with reference to steps 617-619. In an example, the hemodynamic data may include heart sounds (HS) data. One or more HS components, such as a first (S1) heart sound, a second (S2) heart sound, a third (S3) heart sound, or a fourth (S4) heart sound may be detected from the HS sound signal, such as via the signal feature extractor 310 as illustrated in FIG. 3. One or more HS metrics may be generated using the detected HS components. In an example, the HS metrics may include one or more of a S1 intensity or a S2 intensity, which may be measured as S1 amplitude or S2 amplitude, or signal energy of a portion of the HS signal within a S1 window or a S2 window. In another example, the HS metrics may include one or more HS-based cardiac timing intervals.

At 630, one or more of a S1 temporal profile or a S2 temporal profile may be generated. The S1 temporal profile may be generated by trending the S1 intensity measured at multiple cardiac cycles during a time period following the precipitating event. Similarly, the S2 temporal profile may be generated by trending the S2 intensity measured at multiple cardiac cycles during a time period following the precipitating event. S1 intensity is correlated to cardiac contractility, and S2 intensity is correlated to blood pressure. The S1 temporal profile and the S2 temporal profile therefore may represent cardiac and hemodynamic responses following the precipitating event.

At 640, one or more of the S1 temporal profile or the S2 temporal profile may be used to detect syncope, or to classify syncope into one or more syncope categories. A syncope may be detected if the S1 temporal profile or the S2 temporal profile does not show substantial recovery within a specified time period following the precipitating event. In an example, a syncope is detected if the late S1 intensity (or S2 intensity) fails to increase from the early S1 intensity (or S2 intensity) level by an amount exceeding an intensity threshold. In another example, a syncope is detected if the time elapsed for the late S1 intensity (or S2 intensity) to recover to a specified level exceeds a time threshold. In yet another example, a syncope is detected if the trajectory of the S1 intensity (or the trajectory S2 intensity) from the first window $W_I$ to the second window $W_L$ fails to follow an expected recovery pattern within a specific margin.

The detected syncopal event may be classified as a presyncope if the S2 temporal profile satisfies a specified condition, such as the initial S2 intensity during the first window $W_I$ exceeds a threshold (indicating moderate initial blood pressure drop), or the late S2 intensity exceeds the early S1 intensity by an amount exceeding a threshold within a specified time (indicating substantial and relatively timely recovery of blood pressure). In another example, a detected syncopal event may be classified as a cardiogenic syncope if an arrhythmia is detected, or if S1 temporal profile indicates a deterioration of contractility. In another example, the detected syncopal event may be classified into an orthostatic syncope or a neurally mediated syncope using an initial heart sound (HS) vectors and a late HS vector in a vector space.

The syncope classification may include discrimination between an orthostatic syncope and a neurally mediated syncope. The HS response may be represented by at least an initial HS vector $V_I$, and a late HS vector $V_L$. The initial HS vector $V_I$ comprises an initial S1 change $\Delta S1_I$ and an initial S2 change $\Delta S2_I$, denoted by $V_I=(\Delta S1_I, \Delta S2_I)$. The initial HS vector $V_I$ represents composite changes of S1 intensity and S2 intensity from a HS baseline (e.g., prior to a precipitating event) to an initial S1 and S2 intensity measured during an acute phase post precipitating event, such as during a first window $W_I$. The late HS vector $V_L$ comprises a late S1 change $\Delta S1_L$ and a late S2 change $\Delta S2_L$, denoted by $V_L=(\Delta S1_L, \Delta S2_L)$. Various measures of the transition from the initial HS vector $V_I$ to the late HS vector $V_L$ may also be used to discriminate an orthostatic syncope from a neurally mediated syncope. As illustrated in FIGS. 4B-C, an example of such a transition measure is a transition angle $\theta$ between the vector $V_I$ and the vector $V_L$, in a vector space spanned by $\Delta S1$ and $\Delta S2$. The detected syncope may be classified as orthostatic syncope if the angle $\theta$ falls within a range such as between 90 and 180 degrees, or classified as neurally mediated syncope if $\theta$ falls within a range such as between 0 and 90 degrees. Other measures of the transition from $V_I$ to $V_L$ may also be used to discriminate between an orthostatic syncope and a neurally mediated syncope.

The syncope detection or syncope classification information may be provided to a user or a process. If at 650 the syncope is detected and the hypotension is not resolved, hemodynamic monitoring may be continued at 630 to update the S1 temporal profile and S2 temporal profile. If at 650 the syncope is not detected, or the hypotension has been resolved (e.g., adequate hemodynamic recovery), then the hemodynamic monitoring such as S1 temporal profile and S2 temporal profile update may be terminated, and the physiological sensing may be resumed to detect precipitating events for syncope at one of 614-616. In some examples, information about the syncope detection or the syncope classification may be stored in patient medical history, and to update the patient syncope indication or risk at 601. As a result, different precipitating events may be detected for future detecting and evaluating future syncope events.

Figure 7:
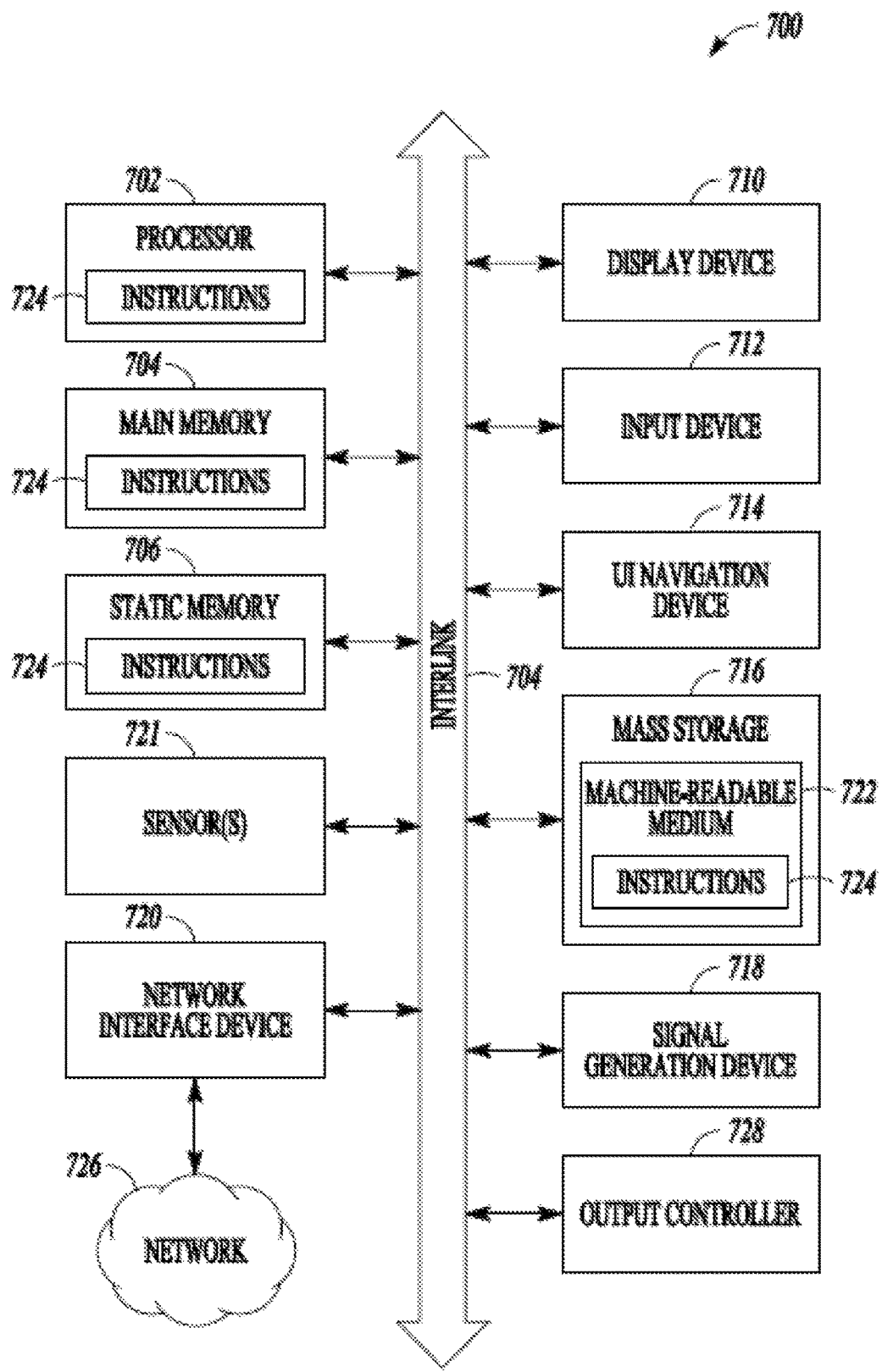
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the AMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for monitoring a patient for syncope, the system comprising:
   a physiological event detector circuit configured to detect a precipitating event associated with a syncope onset using at least one physiological signal;
   a hemodynamic sensor circuit configured to sense a hemodynamic signal including a heart sound (HS) signal, the HS signal including first (S1) and second (S2) heart sound components;
   a syncope analyzer circuit configured to detect a syncopal event and classify the detected syncopal event into one of a plurality of syncope categories;
   a control circuit configured to, in response to the detection of the precipitating event:
      trigger the hemodynamic sensor circuit to acquire hemodynamic data from the sensed hemodynamic signal; and
      control the syncope analyzer circuit to detect and classify the syncopal event using a comparison of a first HS signal sensed during a first time window and a second HS signal sensed during a second time window subsequent to the first time window; and
   an output circuit configured to output the detected and classified syncopal event to a user or a process;
   wherein the syncope analyzer circuit is configured to, in response to the detection of the precipitating event:
      generate an initial S1 intensity change ($\Delta S1_I$) from the first HS signal within the first time window subsequent to an onset of the precipitating event, and generate a late S1 intensity change ($\Delta S1_L$) from the second HS signal within the second time window;
      generate an initial S2 intensity change ($\Delta S2_I$) from the first HS signal within the first time window, and generate a late S2 intensity change ($\Delta S2_L$) from the second HS signal within the second time window;
      detect and classify the detected syncopal event using a comparison between (1) an initial HS response vector comprising $\Delta S1_I$ and $\Delta S2_I$ and (2) a late HS response vector comprising $\Delta S1_L$ and $\Delta S2_L$.

2. The system of claim 1, wherein the syncope analyzer circuit is configured to generate a temporal profile of a hemodynamic parameter using the acquired hemodynamic data, and to detect and classify the syncopal event using the temporal profile of the hemodynamic parameter.

3. The system of claim 2, wherein the temporal profile of the hemodynamic parameter includes an initial measurement of the hemodynamic parameter within the first time window subsequent to an onset of the precipitating event and a late measurement of the hemodynamic parameter within the second time window subsequent to the first time window.

4. The system of claim 3, wherein the syncope analyzer circuit is configured to compute a transition time from the initial measurement to the late measurement of the hemodynamic parameter, and to classify the detected syncopal event further using the computed transition time.

5. The system of claim 2, wherein the syncope analyzer circuit is configured to:
   generate one or more of a S1 temporal profile or a S2 temporal profile in response to the detection of the precipitating event; and
   detect and classify the syncopal event using the S1 temporal profile or the S2 temporal profile.

6. The system of claim 2, wherein the hemodynamic signal includes a photoplethysmogram (PPG) signal, and the syncope analyzer circuit is configured to:
   generate a temporal profile of a PPG parameter using the PPG signal; and
   detect and classify the syncopal event using the temporal profile of the PPG parameter.

7. The system of claim 1, wherein the hemodynamic signal includes a heart rate (HR) signal, and the syncope analyzer circuit is configured to:
   generate a HR temporal profile in response to the detection of the precipitating event; and
   detect and classify the syncopal event further using the HR temporal profile.

8. The system of claim 1, wherein:
   the physiological event detector circuit is configured to detect a cardiac arrhythmia event using a cardiac electrical activity signal; and
   the control circuit is configured to trigger the hemodynamic sensor circuit to acquire the hemodynamic data in response to the detection of the cardiac arrhythmia event.

9. The system of claim 1, wherein:
   the physiological event detector circuit is configured to detect a postural change using a posture sensor signal; and
   the control circuit is configured to trigger the hemodynamic sensor circuit to acquire the hemodynamic data in response to a detection of a postural change to an upright posture.

10. The system of claim 1, wherein:
    the physiological event detector circuit is configured to detect a heart rate change and a postural change; and
    the control circuit is configured to trigger the hemodynamic sensor circuit to acquire the hemodynamic data in response to a detection of an acute reduction in heart rate accompanied by no substantial postural change.

11. The system of claim 1, wherein the hemodynamic signal includes a cardiac timing interval (CTI), and the syncope analyzer circuit is configured to:
    generate a CTI temporal profile in response to the detection of the precipitating event; and
    detect and classify the syncopal event further using the CTI temporal profile.

12. A non-transitory machine-readable storage medium, comprising a plurality of instructions that, responsive to being executed with processor circuitry of a computing device, cause the computing device to:
    detect a precipitating event associated with a syncope onset using at least one physiological signal;
    acquire hemodynamic data in response to the detection of the precipitating event, the hemodynamic data including heart sound (HS) data, the HS data including first (S1) and second (S2) heart sound intensity data;
    generate an initial HS response vector using first HS data within a first time window subsequent to an onset of the precipitating event, the initial HS response vector comprising an initial S1 intensity change and an initial S2 intensity change;
    generate a late HS response vector using second HS data within a second time window subsequent to the first time window, the late HS response vector comprising a late S1 intensity change and a late S2 intensity change;
    detect a syncopal event using the acquired hemodynamic sensor data; and classify the detected syncopal event into one of a plurality of syncope categories using a comparison between the initial HS response vector and the late HS response vector.

13. The non-transitory machine-readable storage medium of claim 12, further comprising an instruction that causes the computing device to:
generate a temporal profile of a hemodynamic parameter using the acquired hemodynamic data; and
detect and classify the syncopal event using the temporal profile of the hemodynamic parameter.

14. A method for monitoring a patient for syncope using a syncope monitor, the method comprising:
detecting, via a physiological event detector circuit, a precipitating event associated with a syncope onset using at least one physiological signal;
acquiring hemodynamic data from the patient, via a hemodynamic sensor circuit, in response to the detection of the precipitating event, the hemodynamic data including heart sound (HS) data, the HS data including first (S1) and second (S2) heart sound intensity data;
generating an initial HS response vector using first HS data within a first time window subsequent to an onset of the precipitating event, the initial HS response vector comprising an initial S1 intensity change and an initial S2 intensity change;
generating a late HS response vector using second HS data within a second time window subsequent to the first time window, the late HS response vector comprising a late S1 intensity change and a late S2 intensity change;
detecting a syncopal event via a syncope detector circuit using the acquired hemodynamic sensor data;
classifying the detected syncopal event into one of a plurality of syncope categories via a syncope classifier circuit using a comparison between the initial HS response vector and the late HS response vector; and
outputting the detected and classified syncopal event to a user or a process.

15. The method of claim 14, further comprising generating a temporal profile of a hemodynamic parameter using the acquired hemodynamic data, the temporal profile including: an initial measurement of the hemodynamic parameter within the first time window subsequent to an onset of the precipitating event; and a late measurement of the hemodynamic parameter within the second time window subsequent to the first time window; and
wherein the detecting and classifying the syncopal event is by using the temporal profile of the hemodynamic parameter.

16. The method of claim 14, wherein classifying the detected syncopal event includes one or more syncope categories including:
a presyncope;
a full-blown syncope;
a cardiogenic syncope;
a non-cardiogenic syncope;
a neutrally mediated syncope;
an orthostatic syncope; or
a non-syncope.

17. The method of claim 14, wherein the precipitating event includes one or more of:
a cardiac arrhythmia event;
a postural change to an upright posture;
a sustained upright posture with physical inactivity; or
an acute reduction in heart rate with no substantial postural change.

18. The method of claim 14, further comprising adjusting one or more parameters for sensing the hemodynamic signal or for acquiring hemodynamic data in response to the detection of the precipitating event.

19. The method of claim 14, wherein the hemodynamic signal includes a cardiac timing interval (CTI), the method comprising:
generating a CTI temporal profile in response to the detection of the precipitating event; and
detecting and classifying the syncopal event further using the CTI temporal profile.

20. The method of claim 14, wherein the hemodynamic signal includes a photoplethysmogram (PPG) signal, the method comprising:
generating a temporal profile of a PPG parameter using the PPG signal in response to the detection of the precipitating event; and
detecting and classifying the syncopal event using the temporal profile of the PPG parameter.

* * * * *